(12) United States Patent  
Wakamiya et al.

(10) Patent No.: US 8,071,029 B2  
(45) Date of Patent: Dec. 6, 2011

(54) SAMPLE ANALYZER AND SAMPLE ANALYZING METHOD

(75) Inventors: Yuji Wakamiya, Kobe (JP); Tomohiro Okuzaki, Himeji (JP); Hisato Takehara, Kobe (JP)

(73) Assignee: Sysmex Corporation, Kobe (JP)

( * ) Notice: Subject to any disclaimer, the term of this patent is extended or adjusted under 35 U.S.C. 154(b) by 684 days.

(21) Appl. No.: 12/079,798

(22) Filed: Mar. 27, 2008

(65) Prior Publication Data

US 2008/0241937 A1     Oct. 2, 2008

(30) Foreign Application Priority Data

Mar. 30, 2007    (JP) ................................. 2007-093409

(51) Int. Cl.
  *G01N 15/06*    (2006.01)
  *G01N 33/00*    (2006.01)
  *G01N 33/48*    (2006.01)

(52) U.S. Cl. ............. 422/68.1; 422/50; 422/63; 422/64; 422/65; 422/66; 422/67; 422/81; 422/82.05; 436/43; 436/47; 436/54; 436/63; 436/66; 436/68; 436/69; 436/70; 436/71; 436/174; 436/180

(58) Field of Classification Search ................. 422/50, 422/63, 64, 65, 66, 67, 81, 82.01, 82.05, 422/68.1; 436/43, 47, 54, 63, 66, 67, 68, 436/69, 70, 71, 174, 180

See application file for complete search history.

(56) References Cited

U.S. PATENT DOCUMENTS

| | | | |
|---|---|---|---|
| 2004/0101440 A1* | 5/2004 | Ishizawa et al. | 422/64 |
| 2005/0047964 A1* | 3/2005 | Nishida et al. | 422/64 |
| 2005/0053521 A1* | 3/2005 | Hirayama | 422/67 |
| 2005/0196821 A1* | 9/2005 | Monfre et al. | 435/14 |
| 2006/0029520 A1* | 2/2006 | Tanoshima et al. | 422/63 |
| 2006/0210438 A1* | 9/2006 | Nagai et al. | 422/73 |
| 2007/0078631 A1* | 4/2007 | Ariyoshi et al. | 702/189 |
| 2007/0110617 A1* | 5/2007 | Nagai et al. | 422/65 |
| 2008/0056944 A1* | 3/2008 | Nakamura et al. | 422/67 |
| 2008/0187951 A1* | 8/2008 | Nagai et al. | 435/29 |
| 2008/0206098 A1* | 8/2008 | Tsutsumida et al. | 422/67 |
| 2009/0035873 A1* | 2/2009 | Shibata | 436/179 |

FOREIGN PATENT DOCUMENTS

JP          09-043244        2/1997

* cited by examiner

*Primary Examiner* — Brian J Sines  
(74) *Attorney, Agent, or Firm* — Brinks Hofer Gilson & Lione

(57) ABSTRACT

A sample analyzer and sample analyzing method perform following: a) mixing a sample with at least one of a first reagent and a second reagent, thereby preparing a measurement specimen; b) storing, in a memory, standard curve data corresponding to a reagent to be used in the step a) for preparing a measurement specimen; c) measuring the measurement specimen thereby obtaining measurement data; d) processing the measurement data based on the standard curve data, thereby obtaining an analysis result; and e) when the first, reagent and the second reagent are of the same type, determining a reagent to be used for the measuring between the first reagent and the second reagent, based on information regarding standard curve data stored in the memory.

12 Claims, 36 Drawing Sheets

Fig. 35

R1/R3, R2 reagent replacement

R1/R3, R2 (Set) | R1/R3 (Individual) | R2 (Individual)

| R-item | Lot No. | Opened date | Remaining quantity (number of times) |
|---|---|---|---|
| HBsAg | ZA9999 | 2006/03/25 | 1 |
| HBsAg | QQ0001 | 2006/03/26 | 200 |
| HBeAg | QQ0003 | 2006/01/10 | 10 |
| HCV | QQ0003 | 2006/01/10 | 11 |
| HBcAb | QQ0004 | 2006/01/10 | 12 |
| HCV | QQ0005 | 2006/01/10 | 13 |
| HCV | QQ0006 | 2006/02/10 | 100 |
| HCV | QQ0007 | 2006/02/10 | 100 |
| HCV | QQ0008 | 2006/02/15 | 100 |
| HIV | QQ0009 | 2006/01/15 | 9 |
| HIV | QQ0010 | 2006/01/30 | 100 |
| Buffer | SS0100 | 2006/01/10 | 100 |

Replace — 202
Retrieve — 203
Close

SAMPLE ANALYZER AND SAMPLE ANALYZING METHOD

RELATED APPLICATIONS

This application claims priority under 35 U.S.C. §119 to Japanese Patent Application No. 2007-093409 filed Mar. 30, 2007, the entire contents of which are hereby incorporated by reference.

TECHNICAL FIELD

The present invention relates to a sample analyzer for analyzing a sample such as an immunological analyzer and a blood coagulation analyzer.

BACKGROUND

In numerous sample analyzers including immunological analyzer and blood coagulation analyzer, a plurality of reagents is used to measure a great number of analyzing items. Each reagent may be used for only one analyzing item or may be used in a plurality of analyzing items, and thus the consuming amount differs among reagents. Regarding the reagents which consuming amount is relatively large, a plurality of reagent containers is held in the reagent container holder of the sample analyzer to prevent the reagent from running out in the middle of the analyzing process thereby causing measurement error. Regarding the usage order of the same reagent accommodated in the plurality of reagent containers, it is proposed to start using from the reagent container with small reagent remaining quantity at the start of operation of the apparatus (see Japanese Laid-Open Patent Publication No. H9-43244).

In sample analyzers, the measurement specimen in which the sample and the reagent are mixed is measured, and the obtained measurement data is converted based on the standard curve corresponding to the used reagent to obtain the analysis result. Therefore, if the standard curve does not exist, the analysis result cannot be obtained, but due to reasons of (1) measurement of a calibrator must be performed when creating the standard curve, and in the meantime, the sample cannot be measured; and (2) the sample measurement is desirably completed at an early stage to send the sample to the next examination in the screening system, measurement is sometimes performed using the reagent which standard curve is not created. In this case, the analysis result cannot be obtained until the standard curve is created, and for example, determination on whether or not re-examination is necessary cannot be made right after the measurement.

Due to the problems in reagent management, error may occur on the standard curve itself. In this case, measurement is performed using the reagent which standard curve is not created, and when the existence of error in the standard curve of the relevant reagent becomes apparent afterwards, the measurement performed up to that point as well as the samples and the reagents used for the measurement become a waste.

The presence of standard curve thus has an important meaning in the analyzing process of the sample, but a sample analyzer that determines the usage order of the reagent based on the presence of the standard curve when a plurality of the same reagents exist in the apparatus did not exist in the prior art.

SUMMARY

The scope of the present invention is defined solely by the appended claims, and is not affected to any degree by the statements within this summary.

A first sample analyzer embodying features of the present invention includes: a reagent container holder for holding a first reagent container accommodating a first reagent and a second reagent container accommodating a second reagent; a measurement specimen preparer for mixing a sample with at least one of the first reagent and the second reagent, thereby preparing a measurement specimen; a memory for storing standard curve data corresponding to a reagent to be used by the measurement specimen preparer for preparing a measurement specimen; a measuring unit for measuring the measurement specimen thereby obtaining measurement data; a measurement data processing means for processing the measurement data based on the standard curve data, thereby obtaining an analysis result; and a reagent determination means, when the first reagent and the second reagent are of the same type, for determining a reagent to be used for the measuring between the first reagent and the second reagent, based on information regarding standard curve data stored in the memory.

A first sample analyzing method embodying features of the present invention includes steps of: a) mixing a sample with at least one of a first reagent and a second reagent, thereby preparing a measurement specimen; b) storing, in a memory, standard curve data corresponding to a reagent to be used in the step a) for preparing a measurement specimen; c) measuring the measurement specimen thereby obtaining measurement data; d) processing the measurement data based on the standard curve data, thereby obtaining an analysis result; and e) when the first reagent and the second reagent are of the same type, determining a reagent to be used for the measuring between the first reagent and the second reagent, based on information regarding standard curve data stored in the memory.

A second sample analyzing method embodying features of the present invention includes steps of: a) dispensing a reagent from at least one of a plurality of reagent containers and mixing the isolated reagent with a sample, thereby preparing a measurement specimen; b) storing, in a memory, standard curve data corresponding to a reagent to be used for preparing the measurement specimen in the step a); c) measuring the measurement specimen thereby obtaining measurement data; d) processing the measurement data based on the standard curve data, thereby obtaining an analysis result; and e) when the plurality of reagents are of the same type, determining a reagent to be used for the measuring among the plurality of reagents, based on whether standard curve data corresponding to each of the plurality of reagents have been stored in the memory.

BRIEF DESCRIPTION OF THE DRAWINGS

FIG. 35 is an example of a R1/R3, R2 reagent replacement dialogue; and

DETAILED DESCRIPTION OF THE PREFERRED EMBODIMENTS

The embodiments of the sample analyzer of the present invention will be described in detail below with reference to the drawings.

Overall Configuration of the Analyzer

Figure 1:
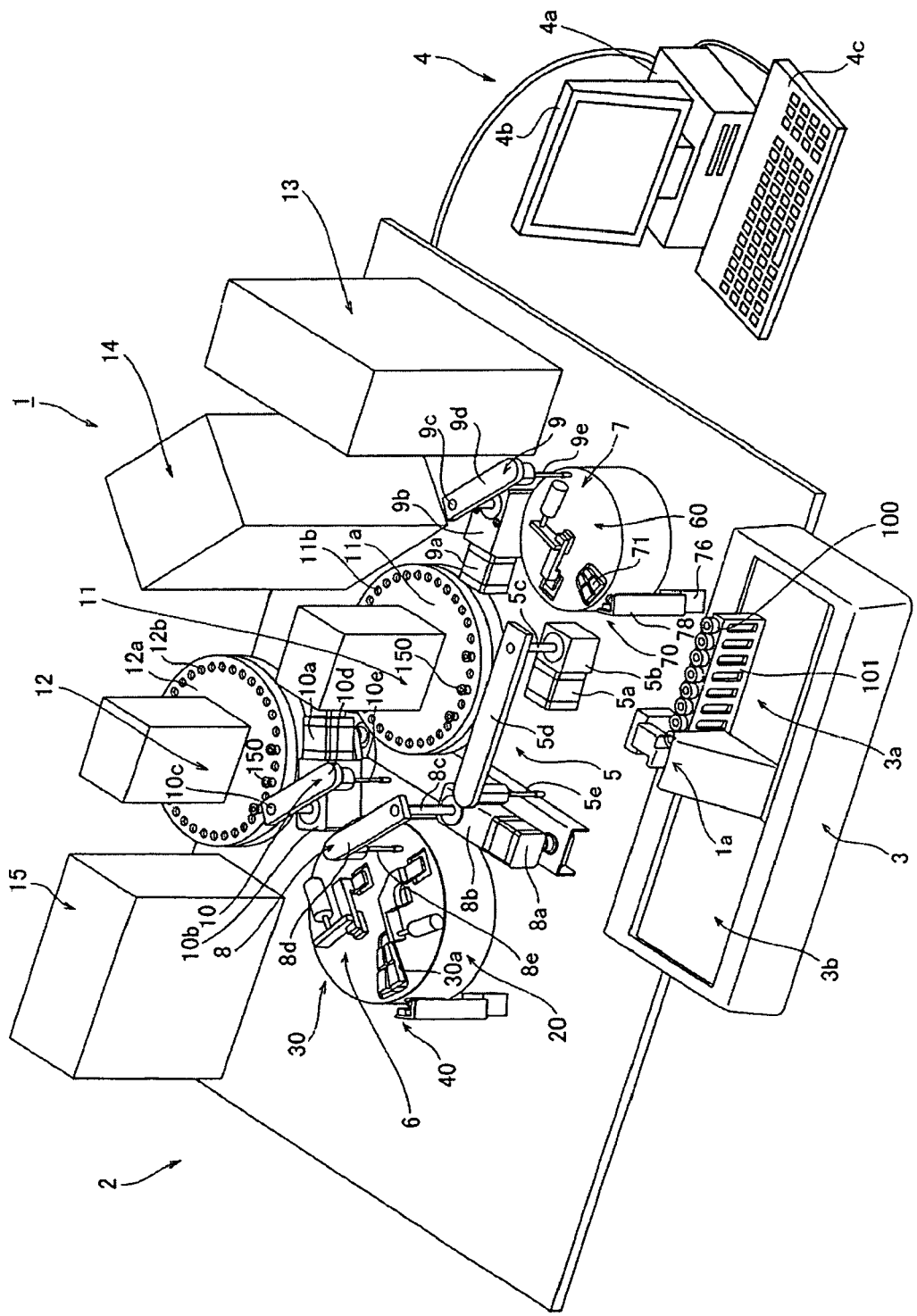
FIG. 1 is a perspective view showing an overall configuration of an immunological analyzer according to one embodiment of the present invention.
Figure 2:
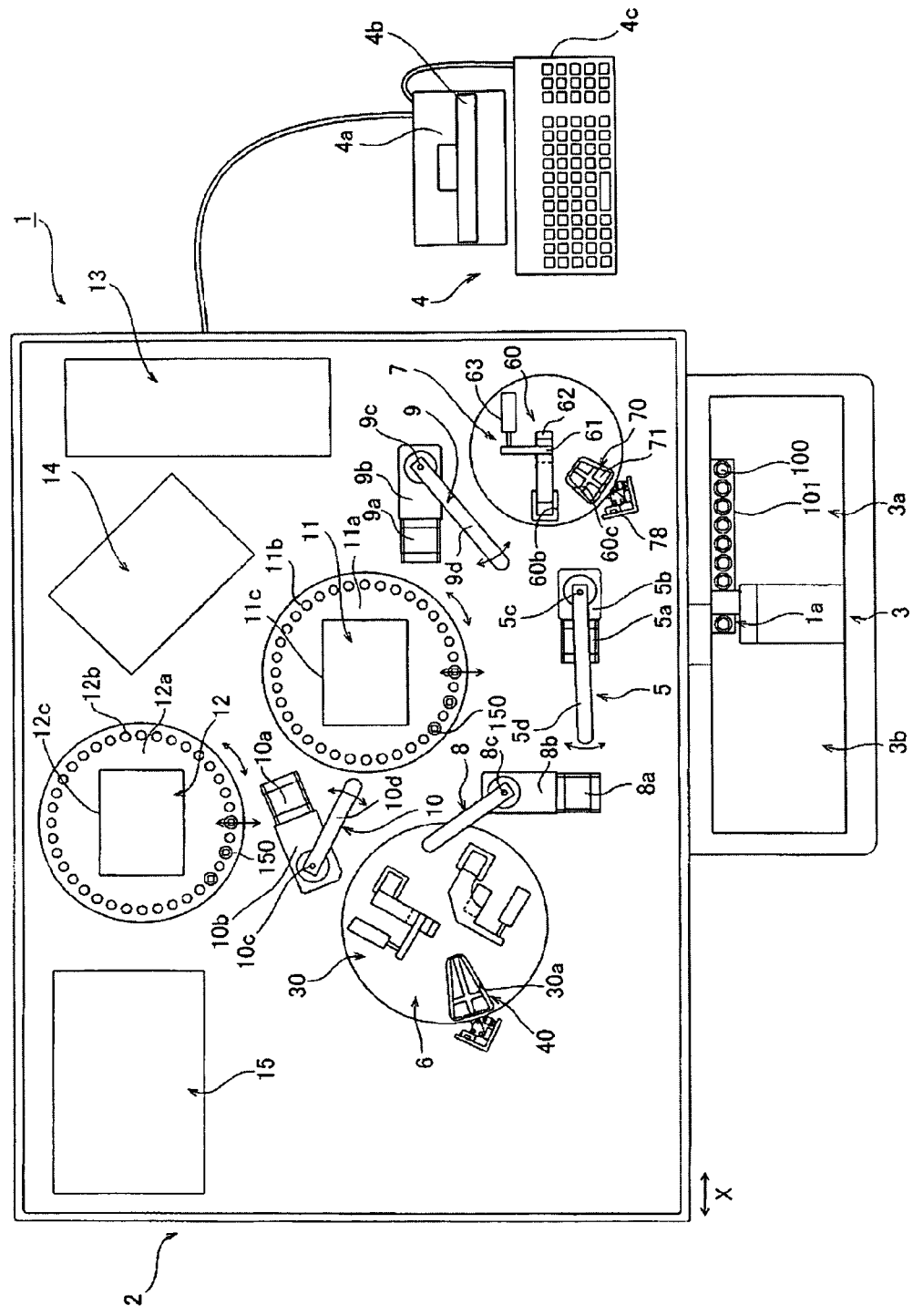
FIG. 2 is a plan view of the immunological analyzer shown in FIG. 1.

FIG. 1 is a perspective view showing an overall configuration of an immunological analyzer 1 according to one embodiment of the present invention, and FIG. 2 is a plan view of the immunological analyzer 1 shown in FIG. 1. The immunological analyzer 1 is an apparatus for carrying out examinations on various items such as hepatitis B, hepatitis C, tumor marker, and thyroid hormone using samples such as blood. In the immunological analyzer 1, magnetic particles (R2 reagent) are bound to a capture antibody (R1 reagent) bound to an antigen contained in a sample such as blood, which is the measuring object, and thereafter, the bound antigen, capture antibody, and magnetic particles are attracted to a magnet (not shown) of a BF (Bound Free) separator 14 (see FIGS. 1 and 2) to remove the R1 reagent containing non-reactive (free) capture antibody. A labeled antibody (R3 reagent) is bound to the antigen bound with magnetic particles, and thereafter, the bound magnetic particles, antigen, and labeled antibody are attracted to a magnet of a BF separator 14 to remove a R3 reagent containing non-reactive (free) labeled antibody. Furthermore, after a light emitting substrate (R5 reagent) that emits light in the reaction process with the labeled antibody is added, a light emitting amount generated through the reaction of the labeled antibody and the light emitting substrate is measured. After such processes, the antigen or the antibody contained in the sample that binds to the labeled antibody is quantitatively measured.

Figure 3:
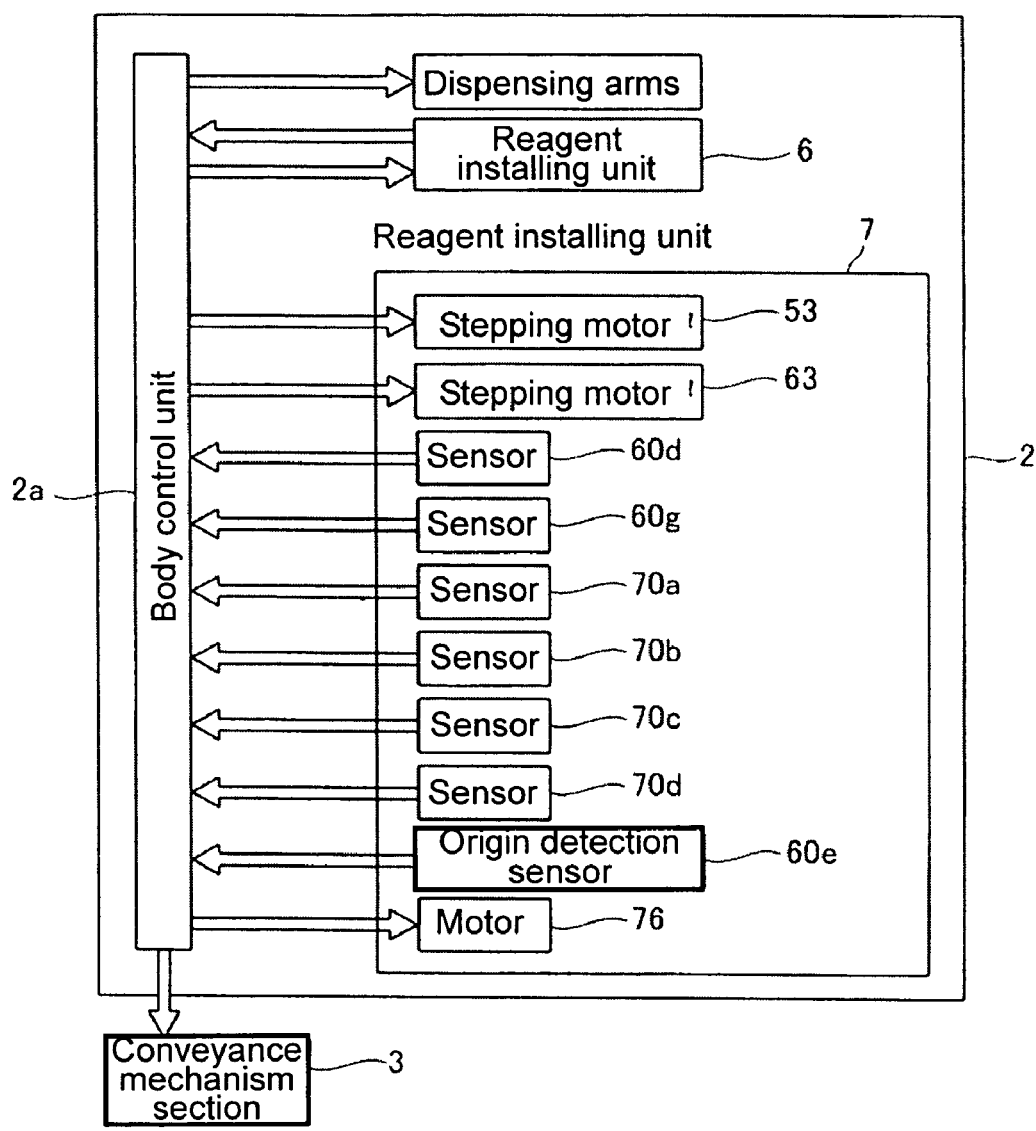
FIG. 3 is a block diagram including a control unit of a measurement mechanism section of the immunological analyzer shown in FIG. 1.

As shown in FIGS. 1 and 2, the immunological analyzer 1 includes a measurement mechanism section 2, a sample conveyance section (sampler) 3 arranged on the front surface side of the measurement mechanism section 2, and a control device 4 including PC (personal computer) electrically connected to the measurement mechanism section 2. The measurement mechanism section 2 is configured by a sample dispensing arm 5, reagent installing units 6 and 7, reagent dispensing arms (reagent aspirating unit) 8, 9, and 10, a primary reaction unit 11 and a secondary reaction unit 12, a cuvette supplying unit 13, a BF separator 14, and a detector 15. As shown in FIG. 3, each mechanism (various dispensing arms, reagent installing unit 6, and reagent installing unit 7, and the like) in the measurement mechanism section 2 are controlled by a body control unit 2a arranged in the measurement mechanism section 2. Specifically, the body control unit 2a receives signals of various sensors (sensors 60d, 60g, 70a, 70b, 70c, 70d, and origin detection sensor 60e, and the like) arranged in the reagent installing unit 7, and controls the drive of various driving sources (stepping motors 53, 63, and motor 76, and the like) arranged in the reagent installing unit 7. The conveyance mechanism section 3 is also controlled by the body control unit 2a. The various dispensing arms, various sensors, and various driving sources will be described in detail below.

Figure 4:
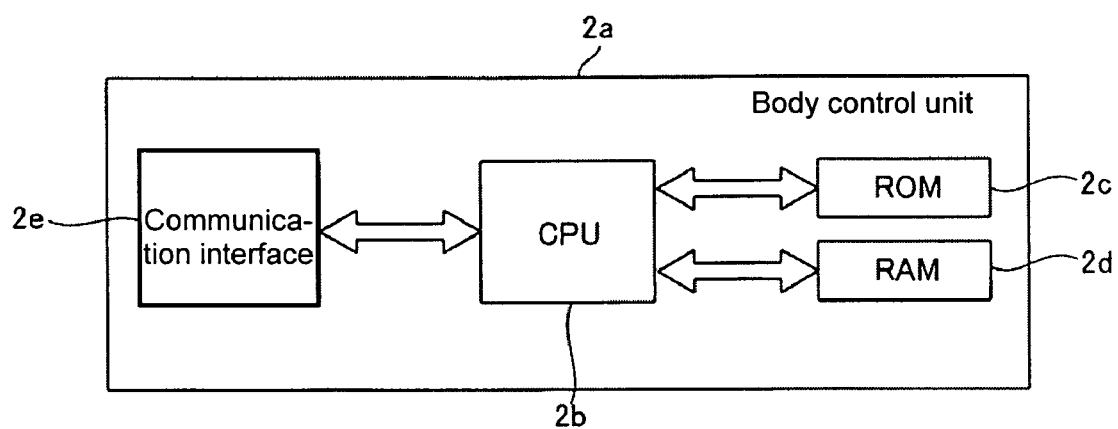
FIG. 4 is a block diagram showing a configuration of the control unit of the measurement mechanism section shown in FIG. 3.

The body control unit 2a is mainly configured by a CPU 2b, a ROM 2c, a RAM 2d, and a communication interface 2e, as shown in FIG. 4.

The CPU 2b can execute computer programs stored in the ROM 2c and the computer programs read by the RAM 2d. The ROM 2c stores computer programs executed by the CPU 2b, data used in executing the computer program, and the like. The RAM 2d is used to read out the computer program stored in the ROM 2c. In executing the computer program, the ROM 2c is used as a work region of the CPU 2b.

The communication interface 2e is connected to the control device 4, and transmits optical information (data of received light amount generated by reaction of the labeled antibody and the light emitting substrate) of the sample to the control device 4, and receives signals from the control unit 4a of the control device 4. The communication interface 2e has a function of transmitting a command from the CPU 2b for driving each unit of the conveyance section 3 and the measurement mechanism section 2.

As shown in FIGS. 1 and 2, the sample conveyance section 3 is configured to convey a rack 101 mounted with a plurality of test tubes 100 accommodating the sample to a position corresponding to an aspirating position 1a where the sample dispensing arm 5 aspirates the sample. The sample conveyance section 3 includes a rack set part 3a for setting the rack 101 in which the test tubes 100 accommodating non-processed sample are mounted, and a rack storing part 3b for storing the rack 101 in which the test tubes 100 accommodating the dispensing processed sample are mounted. The test tube 100 accommodating the non-processed sample is conveyed to a position corresponding to the aspirating position 1a of the sample dispensing arm 5, so that the sample dispensing arm 5 aspirates the sample such as blood in the test tube 100, and thereafter, the rack 101 mounted with the test tube 100 is stored in the rack storing part 3b.

The control device 4 (see FIG. 1) comprises a personal computer (PC), and includes a control unit 4a including CPU, ROM, RAM, a display 4b and a keyboard 4c. The display 4b is arranged to display analysis result obtained by analyzing data of digital signals transmitted from a detector 15, a reagent list listing information related to the reagents described below, and the like. In the present embodiment, the control device 4 is configured so that instruction for replacement, addition, and retrieval of a reagent container 300, as described below, can be carried out in the control device 4.

Figure 5:
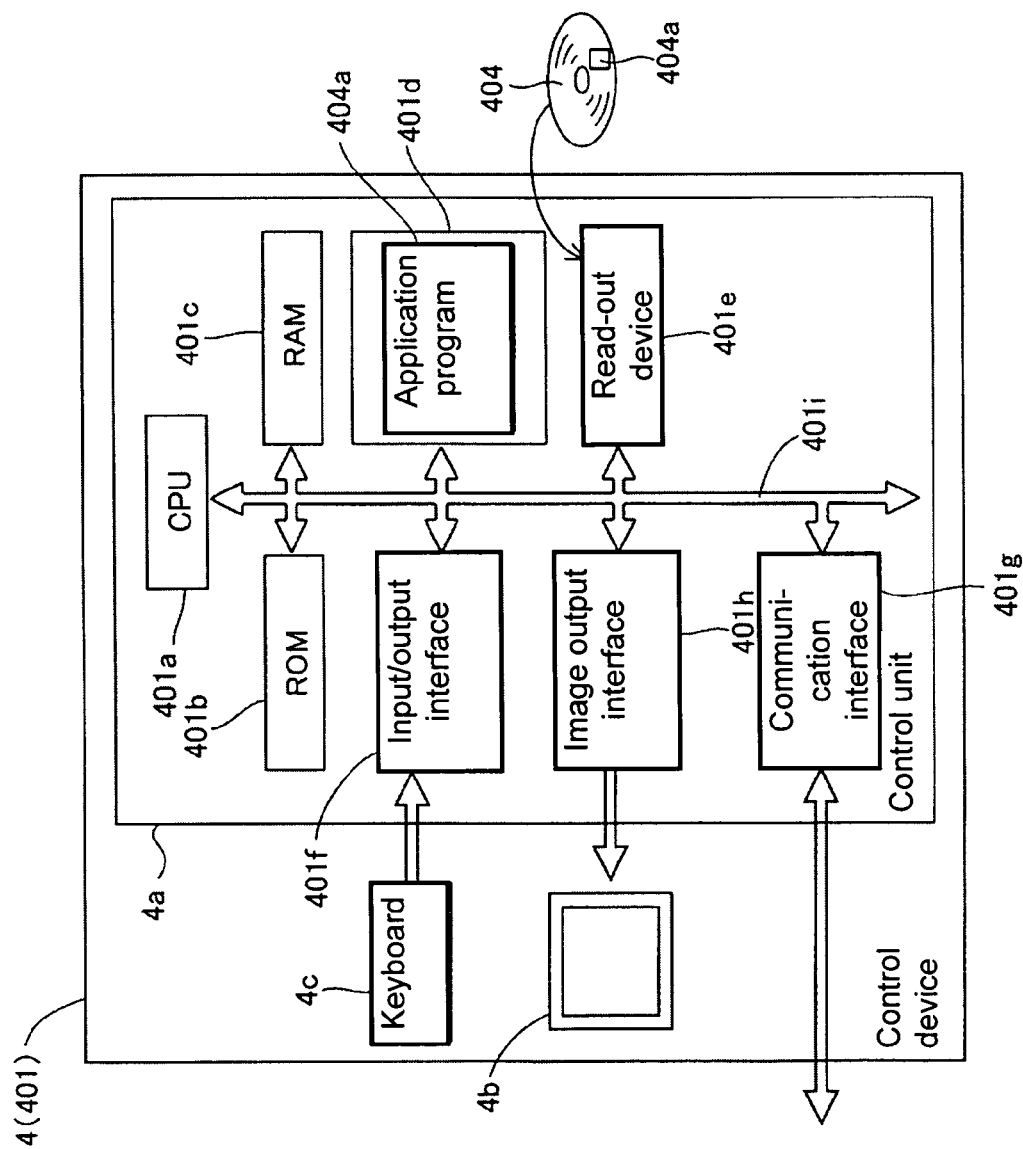
FIG. 5 is a block diagram showing a control device of the immunological analyzer shown in FIG. 1.

The configuration of the control device 4 will now be described. As shown in FIG. 5, the control device 4 is configured by a computer 401 mainly comprising the control unit 4a, the display 4b, and the keyboard 4c. The control unit 4a is mainly configured by a CPU 401a, a ROM 401b, a RAM 401c, a hard disc 401d, a read-out device 401e, an input/output interface 401f, a communication interface 401g, and an image output interface 401h. The CPU 401a, the ROM 401b, the RAM 401c, the hard disc 401d, the read-out device 401e, the input/output interface 401f, the communication interface 401g, and the image output interface 401h are connected by a bus 401i.

The CPU 401a can execute computer programs stored in the ROM 401b and the computer programs loaded in the RAM 401c. The computer 401 serves as the control device 4 when the CPU 401a executes the application program 404a, as described below.

The ROM 401b is configured by mask ROM, PROM, EPROM, EEPROM, and the like, and is recorded with computer programs to be executed by the CPU 401a, data used for the same, and the like.

The RAM 401c is configured by SRAM, DRAM, and the like. The RAM 401c is used to read out the computer programs recorded on the ROM 401b and the hard disc 401d. The RAM 401c is used as a work region of the CPU 401a when executing the computer programs.

The hard disc 401d is installed with various computer programs to be executed by the CPU 401a such as operating system and application program, as well as data used in executing the computer program. The immunological analysis application program 404a according to the present embodiment is also installed in the hard disc 401d.

The read-out device 401e is configured by flexible disc drive, CD-ROM drive, DVD-ROM drive, and the like, and is able to read out computer programs and data recorded on a portable recording medium 404. The immunological analysis application program 404a is stored in the portable recording medium 404, wherein the computer 401 reads out the application program 404a from the portable recording medium 404, and installs the application program 404a to the hard disc 401d.

The application program 404a is not only provided by the portable recording medium 404, and may be provided through telecommunication line (wired or wireless) from external devices communicatably connected with the computer 401 through the telecommunication line. For instance, the application program 404a may be stored in the hard disc of the server computer on the Internet, so that the computer 401 can access the server computer to download the application program 404a and install the application program 404a to the hard disc 401d.

Operating system providing graphical interface environment such as Windows (registered trademark) manufactured and sold by US Microsoft Co. is installed in the hard disc 401d. In the following description, the application program 404a is assumed to operate on the operating system.

The input/output interface 401f is configured by serial interface such as USB, IEEE1394, RS-232C; parallel interface such as SCSI, IDE, IEEE1284; analog interface such as D/A converter, A/D converter, and the like. The keyboard 4c is connected to the input/output interface 401f, so that the user can input data to the computer 401 using the keyboard 4c.

The communication interface 401g is, for example, Ethernet (registered trademark) interface. The computer 401 transmits and receives data with the measurement mechanism section 2 using a predetermined communication protocol by means of the communication interface 401g.

The image output interface 401h is connected to the display 4b configured by LCD, CRT, or the like, and is configured to output an image signal corresponding to the image data provided from the CPU 401a to the display 4b. The display 4b displays the image (screen) according to the input image signal.

The immunological analysis application program 404a installed in the hard disc 401d of the control unit 4a measures the amount of antigen or antibody in the measurement specimen using the received light amount (data of digital signal) of the measurement specimen transmitted from the detector 15 of the measurement mechanism section 2.

The sample dispensing arm 5 (see FIGS. 1 and 2) has a function of dispensing the sample in the test tube 100 conveyed to the aspirating position 1a by the sample conveyance section 3 into a cuvette 150 held by a holder 11b of a rotatable table 11a of the primary reaction unit 11 described below. As shown in FIGS. 1 and 2, the sample dispensing arm 5 includes a motor 5a, a drive transmission part 5b connected to the motor 5a, and an arm 5d attached to the drive transmitting part 5b by way of a shaft 5c. The drive transmitting part 5b is configured to turn the arm 5d around the shaft 5c by the driving force from the motor 5a, and move the arm in the up and down direction (Z direction). A pipette 5e for aspirating and discharging the sample is arranged at the distal end of the arm 5d.

The reagent installing unit 6 (see FIGS. 1 and 2) is arranged to install the reagent container for holding a reagent container in which an R1 reagent containing capture antibody is accommodated and a reagent container in which a R3 reagent containing labeled antibody is accommodated. As shown in FIG. 1, the reagent installing unit 6 includes a reagent holder 20 for holding the reagent container, a lid 30 attached to the reagent holder 20, and a raising and lowering part 40 for replacing the reagent container in the reagent holder 20 through a hole 30a formed in the lid 30.

The reagent installing unit 7 (see FIGS. 1 and 2) is arranged to install a reagent container 300 (see FIG. 6) for holding a reagent container in which a R2 reagent containing magnetic particles is accommodated. The configuration of the reagent installing unit 7 will be described in detail below.

The reagent dispensing arm 8 (see FIGS. 1 and 2) has a function of aspirating the R1 reagent in the reagent container installed in the reagent installing unit 6 and dispensing the aspirated R1 reagent into the cuvette 150 dispensed with the sample of the primary reaction unit 11. The reagent dispensing arm 8 includes a motor 8a, a drive transmission part 8b connected to the motor 8a, and an arm 8d attached to the drive transmitting part 8b by way of a shaft 8c. The drive transmitting part 8b is configured to turn the arm 8d around the shaft 8c by the driving force from the motor 8a, and move the arm in the up and down direction. A pipette 8e (see FIG. 1) for aspirating and discharging the R1 reagent in the reagent container is arranged at the distal end of the arm 8d. That is, the pipette 8e is configured to aspirate the R1 reagent in the reagent container installed in the reagent installing unit 6, and thereafter, dispense the aspirated R1 reagent into the cuvette 150 dispensed with the sample of the primary reaction unit 11.

The reagent dispensing arm 9 (see FIGS. 1 and 2) has a function of dispensing the R2 reagent in the reagent container 300 installed in the reagent installing unit 7 into the cuvette 150 dispensed with the sample and the R1 reagent of the primary reaction unit 11. The reagent dispensing arm 9 includes a motor 9a, a drive transmission part 9b connected to the motor 9a, and an arm 9d attached to the drive transmitting part 9b by way of a shaft 9c. The drive transmitting part 9b is configured to turn the arm 9d around the shaft 9c by the driving force from the motor 9a, and move the arm in the up and down direction. A pipette 9e (see FIG. 1) for aspirating and discharging the R2 reagent in the reagent container 300 is arranged at the distal end of the arm 9d. Thus, the pipette 9e is configured to aspirate the R2 reagent in the reagent container 300 installed in the reagent installing unit 7, and thereafter, dispense the aspirated R2 reagent into the cuvette 150 dispensed with the sample and the R1 reagent of the primary reaction unit 11.

The reagent dispensing arm 10 (see FIGS. 1 and 2) has a function of aspirating the R3 reagent in the reagent container installed in the reagent installing unit 6, and dispensing the aspirated R3 reagent into the cuvette 150 dispensed with the sample, the R1 reagent, and the R2 reagent of the secondary reaction unit 12. The reagent dispensing arm 10 includes a motor 10a, a drive transmission part 10b connected to the motor 10a, and an arm 10d attached to the drive transmitting part 10b by way of a shaft 10c. The drive transmitting part 10b is configured to turn the arm 10d around the shaft 10c by the driving force from the motor 10a, and move the arm in the up and down direction. A pipette 10e (see FIG. 1) for aspirating and discharging the R3 reagent in the reagent container is arranged at the distal end of the arm 10d. That is, the pipette 10e is configured to aspirate the R3 reagent in the reagent container installed in the reagent installing unit 6, and thereafter, dispense the aspirated R3 reagent into the cuvette 150 dispensed with the sample, the R1 reagent, and the R2 reagent of the secondary reaction unit 12.

As shown in FIGS. 1 and 2, the primary reaction unit 11 is arranged to rotatably transfer the cuvette 150 held by the holder 11b of the rotatable table 11a by a predetermined angle for every predetermined period (18 seconds in the present embodiment), and to stir the sample, the R1 reagent, the and the R2 reagent in the cuvette 150. That is, the primary reaction unit 11 is arranged to react the R2 reagent containing magnetic particles and the antigen in the sample in the cuvette 150. The primary reaction unit 11 is configured by a rotatable table 11a for conveying the cuvette 150 accommodating the sample, the R1 reagent, and the R2 reagent in the rotating direction, and a container conveying part 11c for stirring the sample, R1 reagent, and R2 reagent in the cuvette 150 and conveying the cuvette 150 accommodating the stirred sample, R1 reagent and R2 reagent to the BF separator 14 (see FIGS. 1 and 2) described below.

The rotatable table 11a is configured so as to rotatably transfer the cuvette 150 held in the holder 11b by a predetermined angle every 18 seconds. Thus, various devices (sample dispensing arm 5, reagent dispensing arms 8 and 9 etc.) of the immunological analyzer 1 are controlled so as to operate on the cuvette 150 at the predetermined transferred position at a timing the cuvette is transferred to the predetermined position by the rotatable table 11a.

The container conveying part 11c is rotatably arranged at the central portion of the rotatable table 11a. The container conveying part 11c has a function of gripping the cuvette 150 held in the holder 11b of the rotatable table 11a and stirring the sample in the cuvette 150. Furthermore, the container conveying part 11c has a function of transferring the cuvette 150 accommodating the specimen obtained by stirring and incubating the sample, the R1 reagent and the R2 reagent to the BF separator 14 (see FIGS. 1 and 2).

The secondary reaction unit 12 (see FIGS. 1 and 2) has a configuration similar to the primary reaction unit 11, and is arranged to rotatably transfer the cuvette 150 held by the holder 12b of the rotatable table 12a by a predetermined angle for every predetermined period (18 seconds in the present embodiment), and to stir the sample, the R1 reagent, the R2 reagent, the R3 reagent, and the R5l reagent in the cuvette 150. That is, the secondary reaction unit 12 is arranged to react the R3 reagent containing labeled antibody and the antigen in the sample in the cuvette 150, and to react the R5l reagent containing light emitting substrates and the labeled antibody of the R3 reagent. The R5l reagent is dispensed into the cuvette 150 accommodating the sample, the R1 reagent, the R2 reagent, and the R3 reagent of the secondary reaction unit 12 by a R5l reagent dispensing arm (not shown) arranged near the secondary reaction unit 12. The secondary reaction unit 12 is configured by a rotatable table 12a for conveying the cuvette 150 accommodating the sample, the R1 reagent, the R2 reagent, the R3 reagent, and the R5 reagent in the rotating direction, and a container conveying part 12c for stirring the sample, the R1 reagent, the R2 reagent, R3 reagent, and the R5l reagent in the cuvette 150 and conveying the cuvette 150 accommodating the stirred sample etc. to the BF separator 14. Furthermore, the container conveying part 12c has a function of again conveying the cuvette 150 processed by the BF separator 14 to the holder 12b of the rotatable table 12a. The detailed structure of the secondary reaction unit 12 is similar to the primary reaction unit 11, and thus the description thereof will be omitted.

The cuvette supplying unit 13 (see FIGS. 1 and 2) is configured so as to sequentially supply a plurality of cuvettes 150 to the holder 11b of the rotatable table 11a of the primary reaction unit 11.

The BF separator 14 has a function of separating the non-reacting R1 reagent (unnecessary component) and the magnetic particles from the specimen in the cuvette 150 conveyed by the container conveying part 11c of the primary reaction unit 11, and a function of separating the non-reacting R3 reagent (unnecessary component) and the magnetic particles from the specimen in the cuvette 150 (see FIG. 1) conveyed by the container conveying part 12c of the secondary reaction unit 12.

The detector 15 (see FIGS. 1 and 2) is arranged to measure the amount of antigen contained in a sample by obtaining the light generated in the reaction process of the labeled antibody bound to the antigen of the sample performed with a predetermined process and the light emitting substrate with a photo multiplier tube.

The structure of the reagent installing unit 7 of the immunological analyzer 1 and the reagent container 300 installed in the reagent installing unit 7 according to one embodiment of the present invention will now be described with reference to FIGS. 6 to 18.

Figure 6:
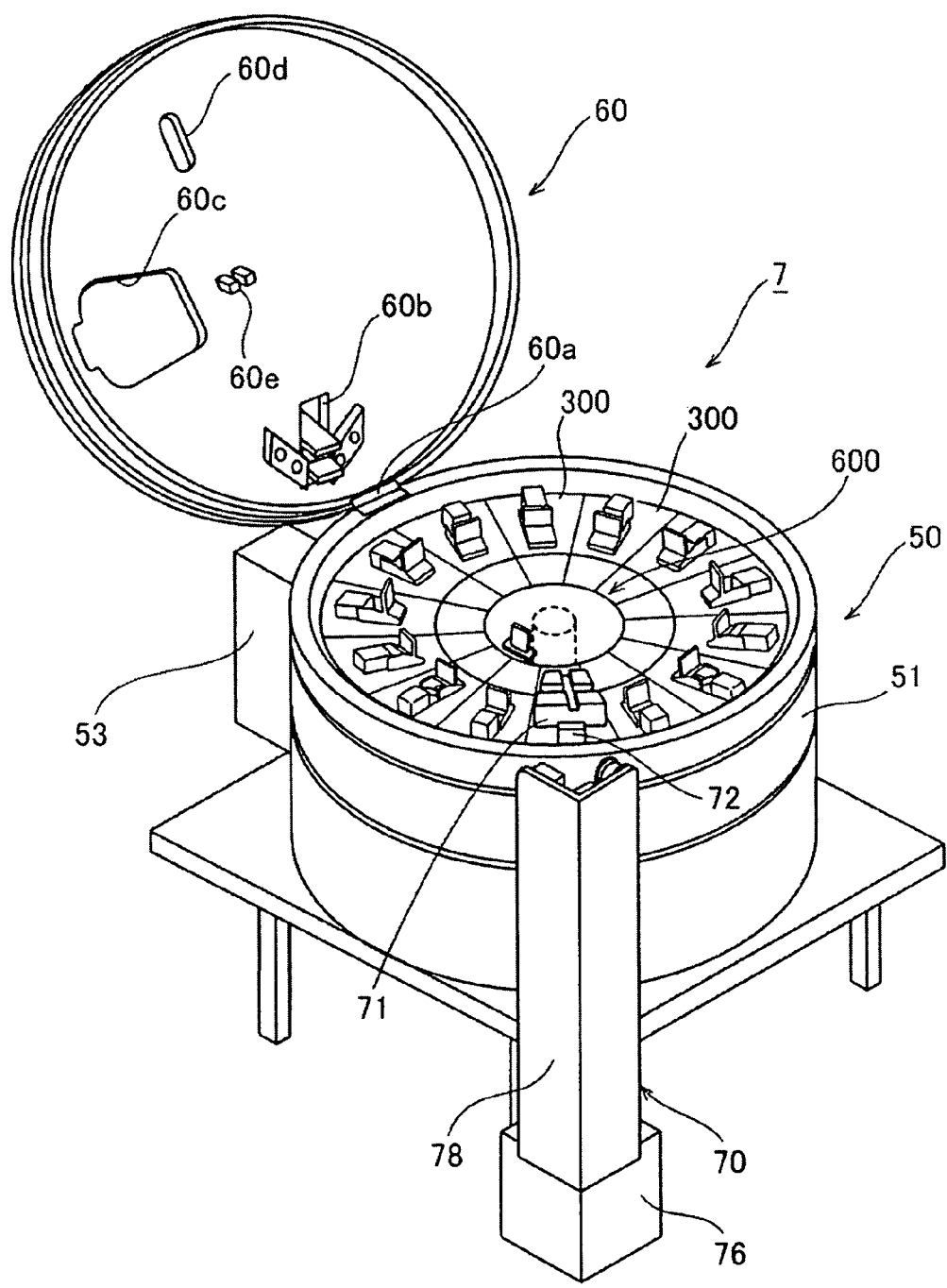
FIG. 6 is a perspective view showing an overall configuration of a reagent installing unit shown in FIG. 1.

As shown in FIG. 6, the reagent installing unit 7 includes a cylindrical reagent holder 50 for holding the reagent container 300 in a circular ring form, a lid 60 attached to the reagent holder 50 in an openable and closable manner, and a raising and lowering part 70 attached to the side surface (outer wall part 51) of the cylindrical reagent holder 50. A Peltier element (not shown) is also attached at the bottom of the reagent installing unit 7, and the inside of the reagent installing unit 7 is maintained at about 15° C.

Figure 7:
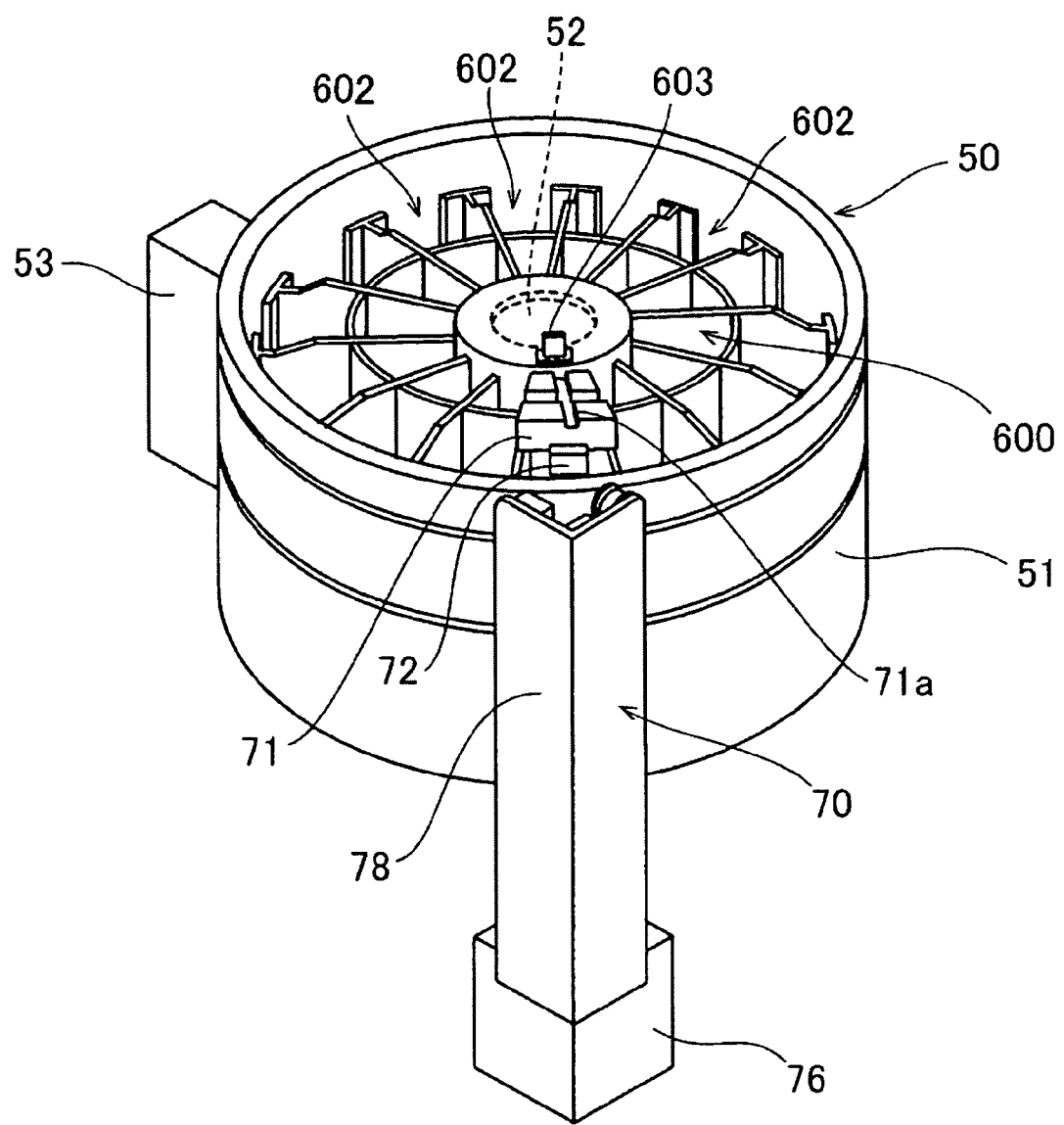
FIG. 7 is a perspective view showing a reagent holder of the reagent installing unit shown in FIG. 6.
Figure 8:
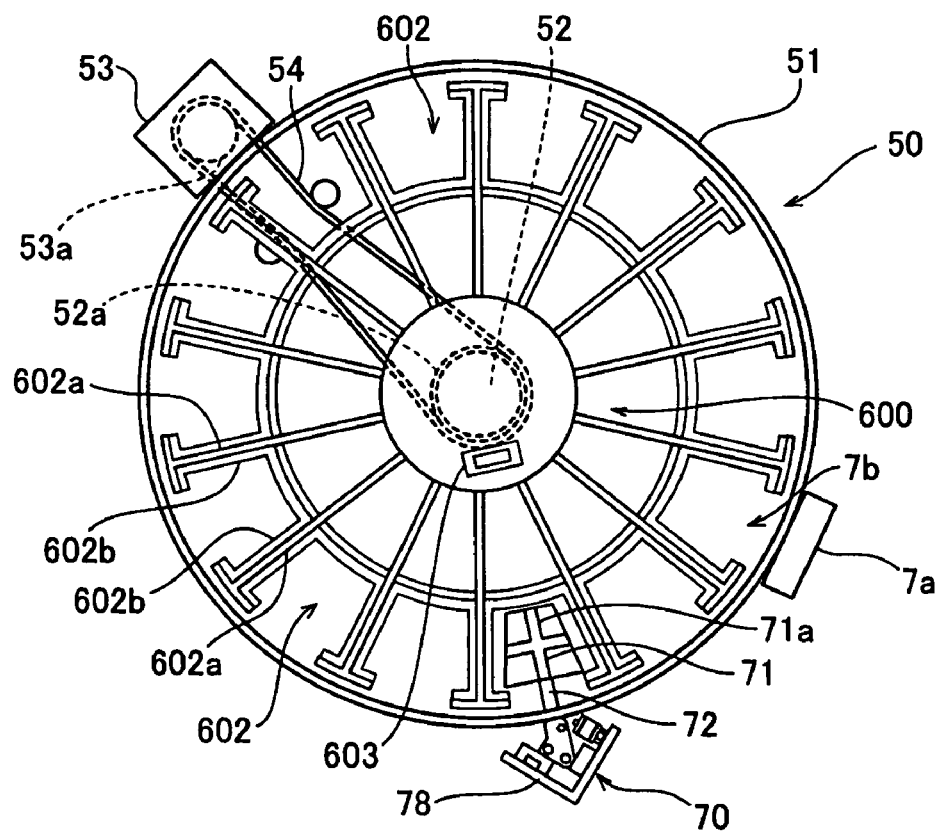
FIG. 8 is a plan view of the reagent holder of the reagent installing unit shown in FIG. 7.

As shown in FIGS. 7 and 8, the reagent holder 50 includes a cylindrical outer wall part 51, a rotatable rotation shaft 52 arranged at the center, a stepping motor 53 for rotating the rotation shaft 52, and a belt 54 for transmitting the driving force of the stepping motor 53 to the rotation shaft 52 (see FIG. 8). A heat insulating material (not shown) is attached over the entire surface on the inner surface of the outer wall part 51, so that the temperature inside the reagent holder 50 is maintained at low temperature (about 15° C.). As shown in FIG. 8, the driving force of the stepping motor 53 is transmitted to the rotation shaft 52 via the belt 54 by a pulley 53a that rotates with the stepping motor 53 and a pulley 52a coaxially fixed to the rotation shaft 52.

Figure 9:
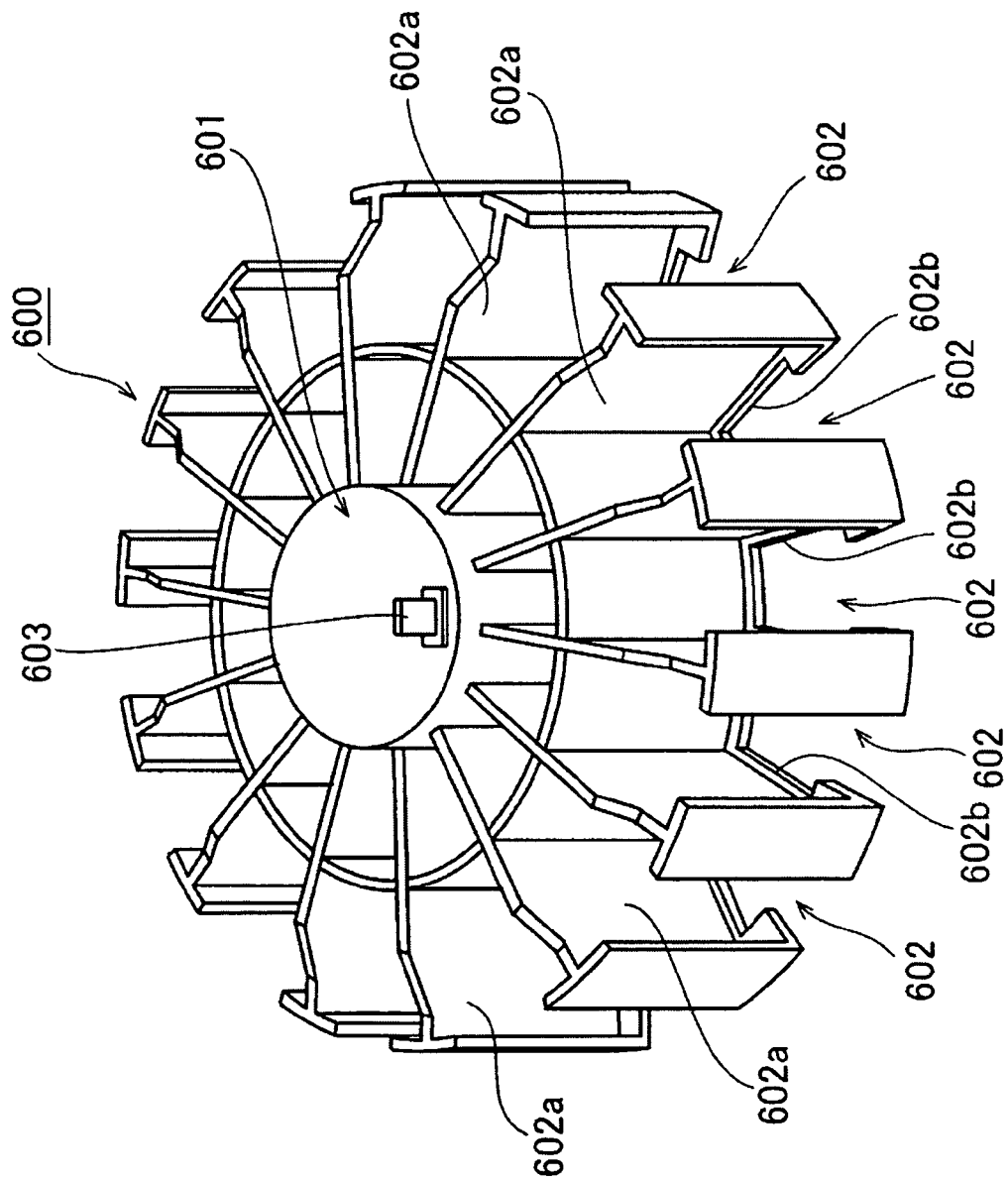
FIG. 9 is a perspective view showing a rack for holding the reagent container used in the immunological analyzer shown in FIG. 1.

A rack 600 for holding a plurality of reagent containers' 300 in a circular ring form is fixedly attached to the rotation shaft 52. The rack 600 holding the reagent containers 300 rotates when the rotation shaft 52 is rotated with the reagent containers 300 held in the rack 600, and thus the reagent container 300 holding the reagent to be aspirated can be moved to below a hole 60b and an input/output hole 60c of the lid 60 described below. As shown in FIG. 9, the rack 600 includes an inserting part 601 formed at the center of the rack 600, to which the rotation shaft 52 is inserted; a plurality of holders 602, formed in a circular ring form around the inserting part 601, for holding the reagent container 300, and an origin detection strip 603 arranged so as to project above the inserting part 601. The holder 602 is configured by a partition plate 602a and a supporting part 602b. The partition plate 602a is arranged in plurals at a predetermined angular interval so as to radially extend from the inserting part 601. The supporting part 602b is arranged at the lower part of the portions facing each other of the partition plates 602a and at the lower part of the inserting part 601 so as to project to the inner side. Each reagent container 300 is arranged such that the peripheral edge of the bottom 323 (see FIG. 18) is supported by the supporting part 602b in a space defined by a pair of partition plates 602a. Furthermore, as shown in FIG. 8, the upper part and the lower part, as well as the outer sides in the radial direction of the holder 602 are formed as open ends, so that a mounting platform 71 and an arm 72 of the raising and lowering part 70 for raising or lowering the reagent container 300 can be raised or lowered without contacting the holder 602 of the rack 600.

The reagent installing unit 7 comprises a reagent information reading unit (barcode reader) 7a. The reagent information reading unit 7a reads a barcode provided with a reagent container set in the reagent installing unit 7.

Figure 10:
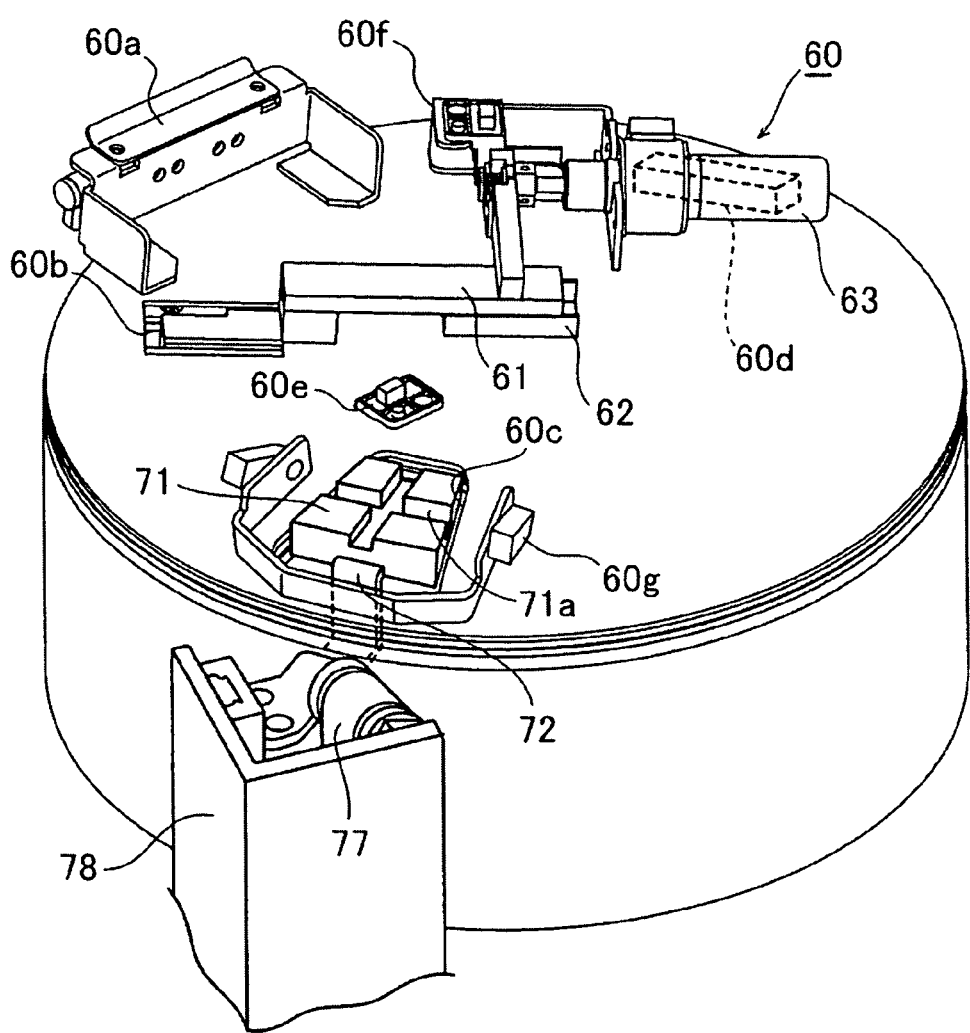
FIG. 10 is a perspective view showing the reagent installing unit shown in FIG. 6.
Figure 11:
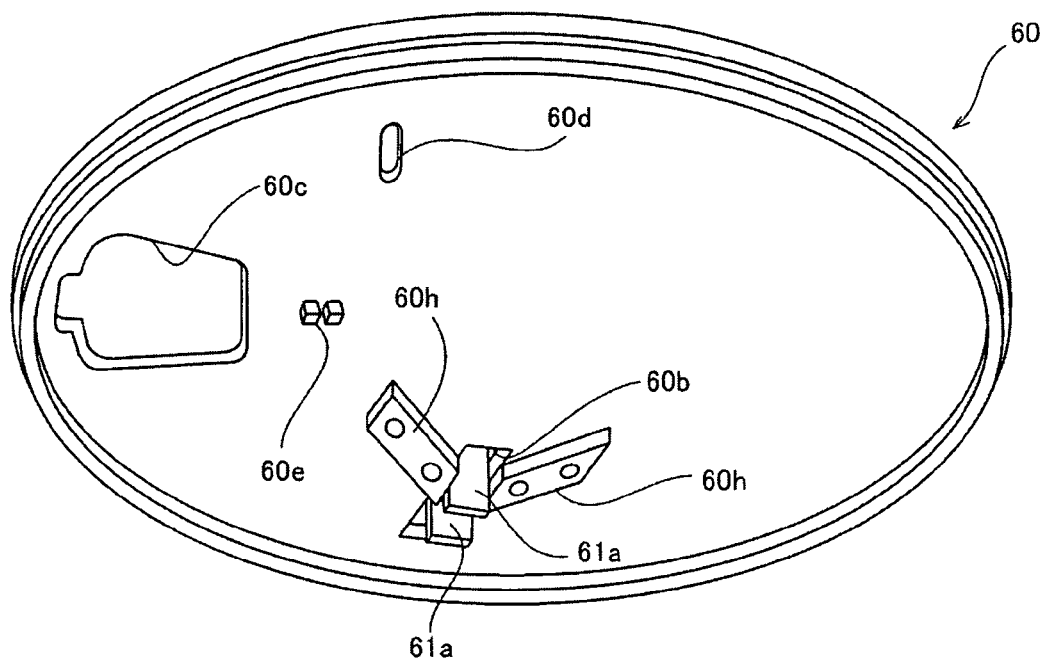
FIG. 11 is a perspective view showing a back surface of a lid of the reagent installing unit shown in FIG. 10.

As shown in FIG. 6, the lid 60 is attached in an openable and closable manner to the reagent holder 50 by way of a hinge part 60a. The lid 60 is configured to shield outside air so that the temperature in the reagent installing unit 7 is maintained at a low temperature (15° C.), and so as to enable the reagent in the reagent installing unit 7 to be aspirated from the outside and the reagent container 300 to be placed in or taken out from the reagent installing unit 7. Specifically, as shown in FIGS. 10 and 11, the lid 60 has the hole 60b to be inserted with a pipette 9e of the reagent dispensing arm 9 when aspirating the reagent from the reagent container 310 (see FIGS. 16 and 17) of the reagent container 300, and the input/output hole 60c for placing in or taking out the reagent container 300 from the reagent installing unit 7 by the raising and lowering part 70. Furthermore, the lid 60 includes an openable/closable member 61 for opening or closing a slide lid 322 (see FIGS. 16 and 17) of the reagent container 300 arranged below the hole 60b, a linear movement guide 62 for slidably supporting the openable/closable member 61, and a stepping motor 63 for driving the openable/closable member 61 in a reciprocating manner. The lid 60 is arranged with a reflection sensor 60d for detecting whether or not the reagent container 300 is held in the holder 602 of the rack 600, a transmissive origin detection sensor 60e for detecting an origin position of the rack 600, a transmissive sensor 60f for detecting an origin position of the openable/closable member 61, and a transmissive sensor 60g for detecting the reagent container 300 mounted on the mounting platform 71 of the raising and lowering part 70 described below. The sensor 60d is arranged on the front surface side of the lid 60 so that light can be irradiated towards the back surface side of the lid 60, and the origin detection sensor 60e is arranged on the back surface side of the lid 60. The sensor 60f is arranged on the front surface side of the lid 60. The sensor 60g is arranged on the front surface side of the lid 60 so as to cross the input/output hole 60c.

As shown in FIG. 11, the openable/closable member 61 includes a two-forked engagement strip 61a similar to an openable/closable member 31. When the reagent container 300 is arranged below the hole 60b with the slide lid 322 closed, the engagement strip 322a (see FIG. 16) of the slide lid 322 of the reagent container 300 is positioned between the two-forked engagement strip 61a of the openable/closable member 61. A pair of guide strips 60h is attached in the vicinity of the hole 60b of the back surface of the lid 60. The pair of guide strips 60h has a function of contacting the engagement strip 322a of the slide lid 322 by the rotation of the rotation shaft 52 and guiding the same when arranged below the hole 60b with the slide lid 322 of the reagent container 300 opened, thereby positioning the engagement strip 322a of the slide lid 322 between the two-forked engagement strip 61a of the openable/closable member 61.

The reflection sensor 60d is configured to detect whether or not the reagent container 300 is held in the holder 602 of the rack 600. The transmissive origin detection sensor 60e has a function of detecting the origin position of the rotating rack 600 by detecting the origin detection strip 603 arranged in the rack 600.

Figure 12:
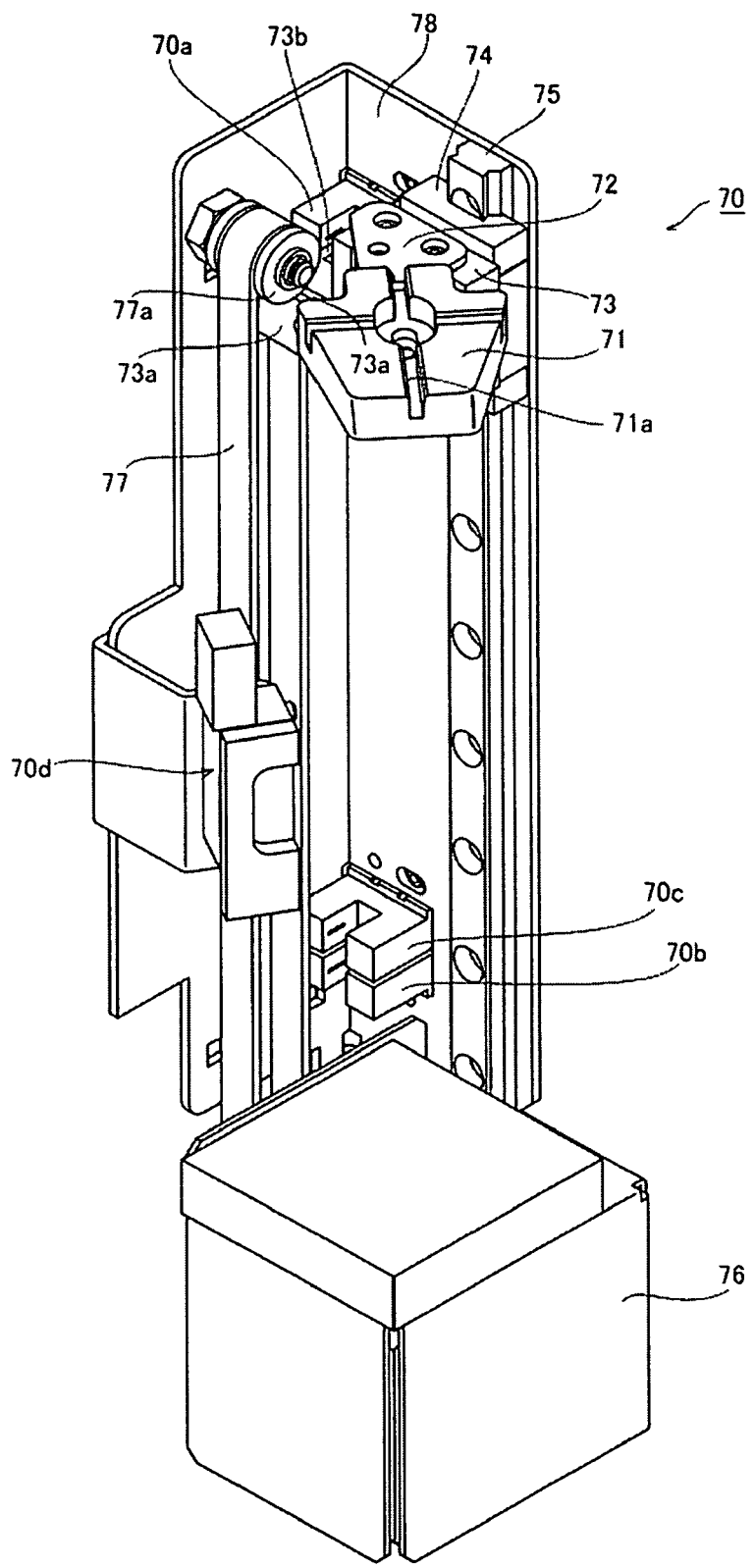
FIG. 12 is a perspective view showing one example of a raising and lowering part.
Figure 13:
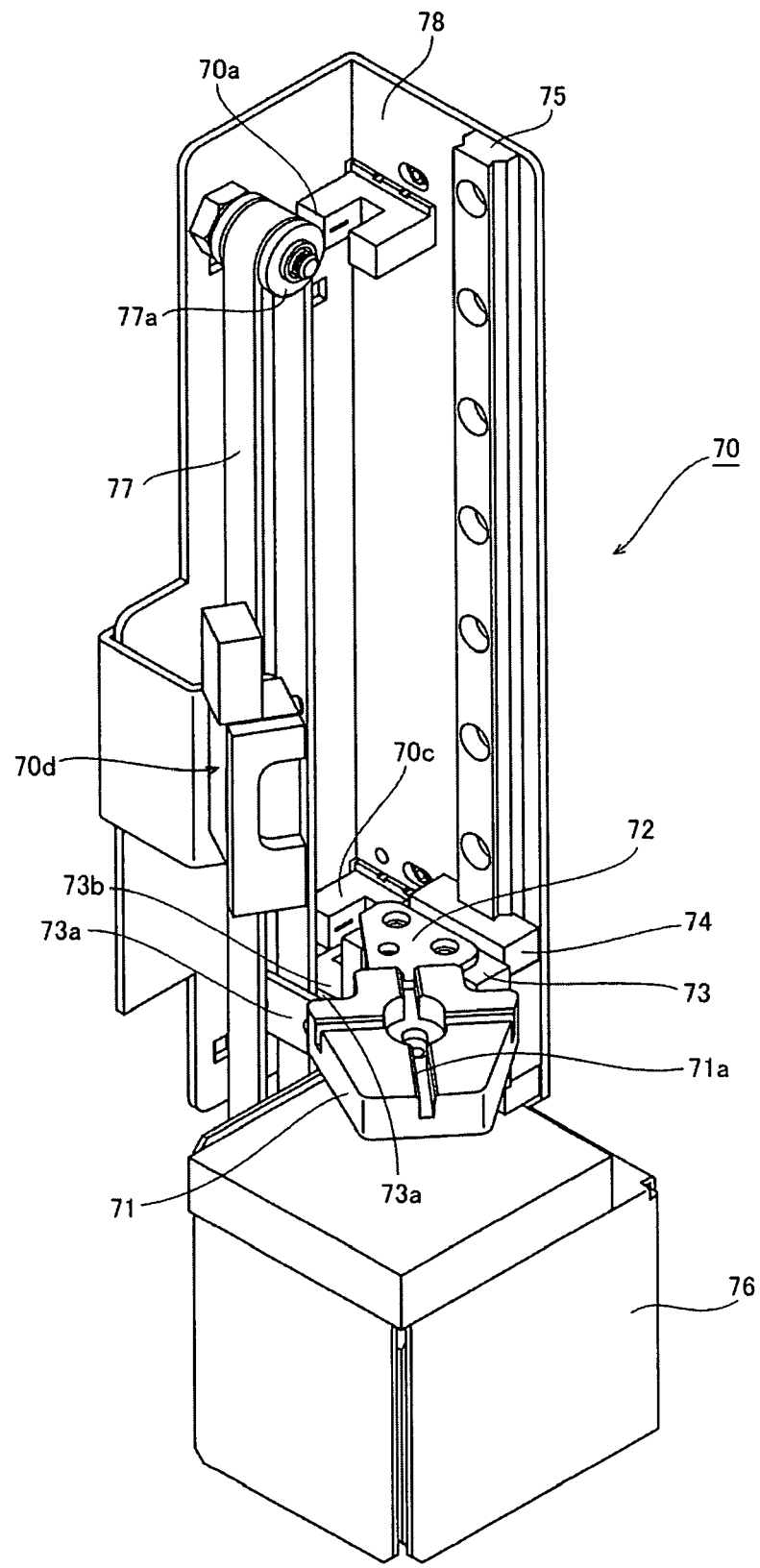
FIG. 13 is a perspective view showing one example of the raising and lowering part.
Figure 14:
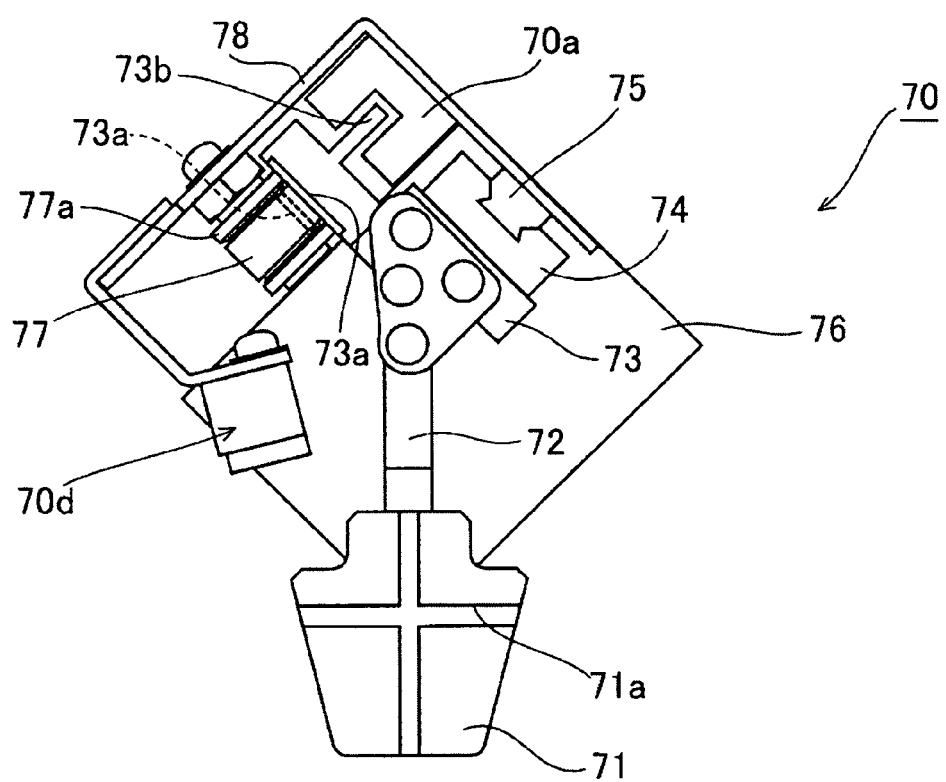
FIG. 14 is a plan view showing one example of the raising and lowering part.

In the present embodiment, the raising and lowering part 70 is arranged to place in and take out the reagent container 300 in the reagent installing unit 7. As shown in FIGS. 12 to 14, the raising and lowering part 70 includes the mounting platform 71 mounted with the reagent container 300, the arm 72 for supporting the mounting platform 71, a supporting member 73 for supporting the arm 72, a linear movement guide including a slider 74 fixed with the supporting member 73 and a guide rail 75 for slidably supporting the slider 74 in the up and down direction, a motor 76, a belt 77 for transmitting the driving force of the motor 76, and a bracket 78. Three transmissive sensors 70a, 70b, and 70c as well as a reflection sensor 70d are attached to the bracket 78.

Figure 15:
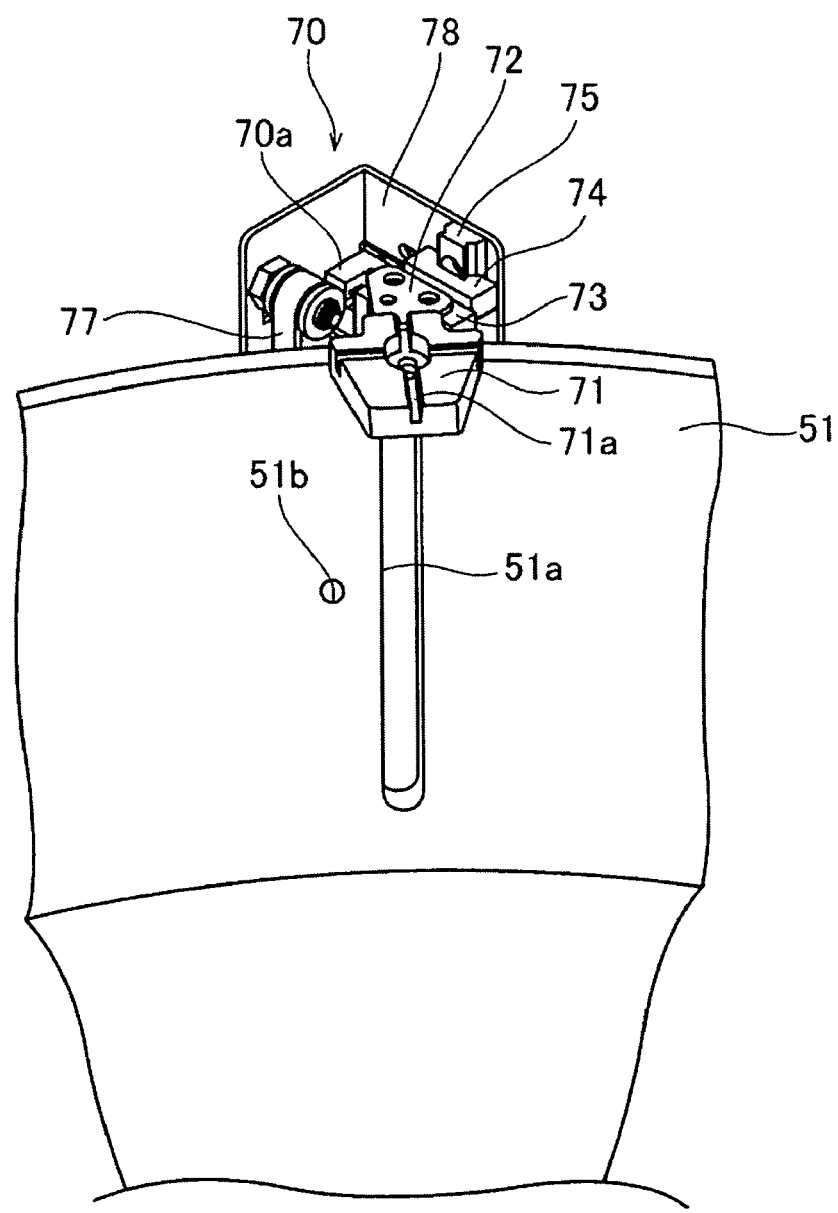
FIG. 15 is a perspective view showing a hole formed in an outer wall part of the reagent holder.

The mounting platform 71 has a function of holding the reagent container 300 in the holder 602 of the rack 600 by being lowered with the reagent container 300 mounted thereon. The mounting platform 71 has a function of lifting the reagent container 300 of the holder 602 and taking out the reagent container 300 from the input/output hole 60c of the lid 60 by being raised from below the holder 602 holding the reagent container 300. A cross-shaped groove 71a that engages with a rib 323a (see FIG. 18) arranged at the bottom 323 of the reagent container 300 is formed in the mounting platform 71. As shown in FIG. 15, the arm 72 has a function of moving the mounting platform 71 in the up and down direction by the driving force of the motor 76 arranged exterior to the reagent holder 50 by way of a hole 51a extending in the up and down direction on the outer wall part 51.

A blocking member (not shown) made of elastic material arranged with a slit that corresponds to the hole 51a is attached to the hole 51a. The arm 72 supports the mounting platform 71 by way of the slit. The blocking member prevents cold air in the container holder 50 from leaking outside from the hole 51a without inhibiting the movement of the arm 72.

As shown in FIG. 14, a two-forked fixing strip 73a arranged on the supporting member 73 is fixed to the belt 77 with the belt 77 in between. The driving force of the motor 76 is transmitted to the supporting member 73 via the belt 77. Furthermore, a detection strip 73b is arranged in a projecting manner on the supporting member 73. The position in the up and down direction of the mounting platform 71 is detected when the detection strip 73b is detected by the sensors 70a, 70b, and 70c. Specifically, when the detection strip 73b is detected by the sensor 70a, the mounting platform 71 is positioned at a mounting/retrieving position (top dead point) at which the reagent container 300 can be mounted and retrieved. When the detection strip 73b is detected by the sensor 70b, the mounting platform 71 is positioned below (bottom dead point) the holder 602 of the rack 600. The mounting platform 71 is arranged below the reagent container 300 held in the rack 600 when positioned at the bottom dead point, whereby the rack 600 can be rotated. A predetermined clearance region is provided between the rack 600 and the bottom dead point, and the sensor 70c detects the detection strip 73b. The control unit 2a can recognize that the mounting platform 71 is positioned in the clearance region between the holder 602 of rack 600 and the bottom dead point. Therefore, when the mounting platform 71 is positioned in the clearance region, the mounting platform 71 and the rack 600 are avoided from contacting each other when the rack 600 is rotated. The belt 77 is configured to be rotatably driven by a pulley (not shown) coaxially arranged on a rotation shaft (not shown) of the motor 76, and a pulley 77a arranged on the upper side.

The reflection sensor 70d detects the reagent container 300 held in the holder 602 of the rack 600 by way of a hole 51b (see FIG. 15) formed in the outer wall part 51 to monitor whether or not the replacement of the reagent container 300 has been properly performed.

Figure 16:
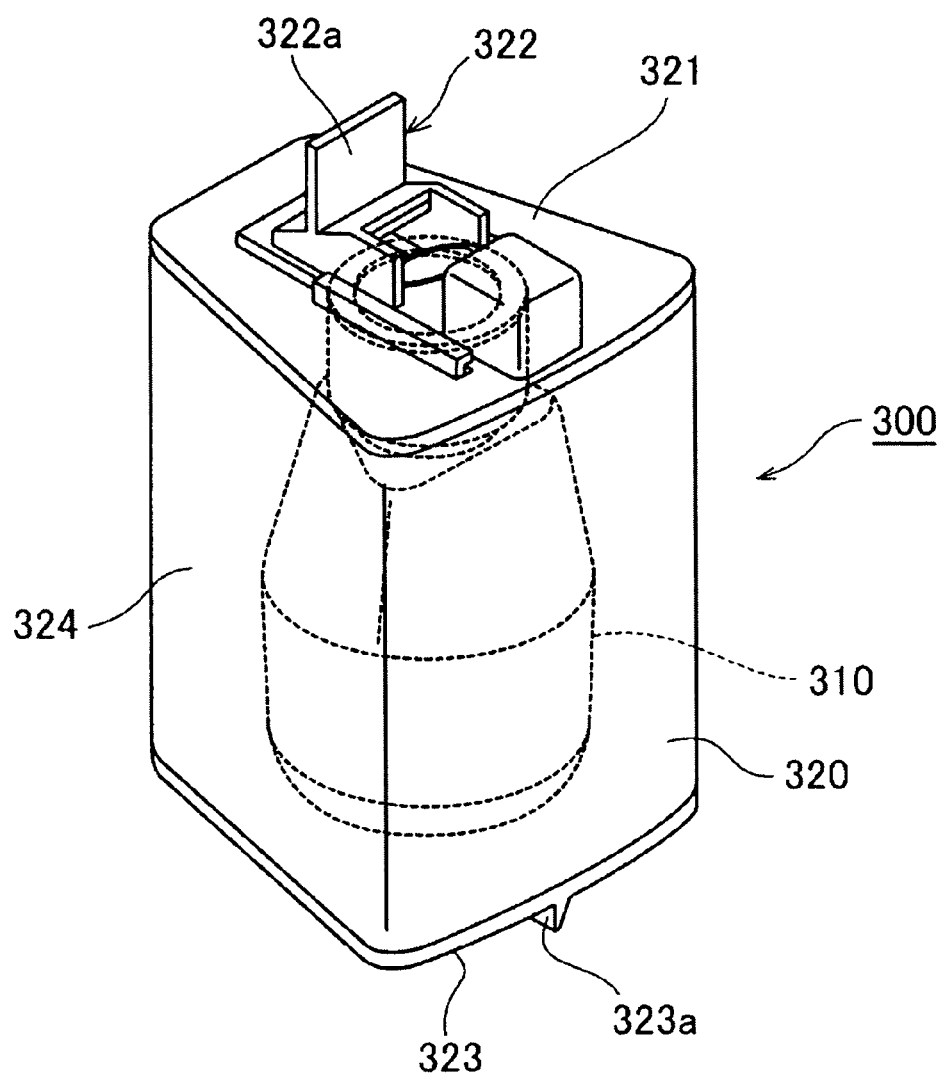
FIG. 16 is an outer appearance view of the reagent container used in the immunological analyzer shown in FIG. 1.
Figure 17:
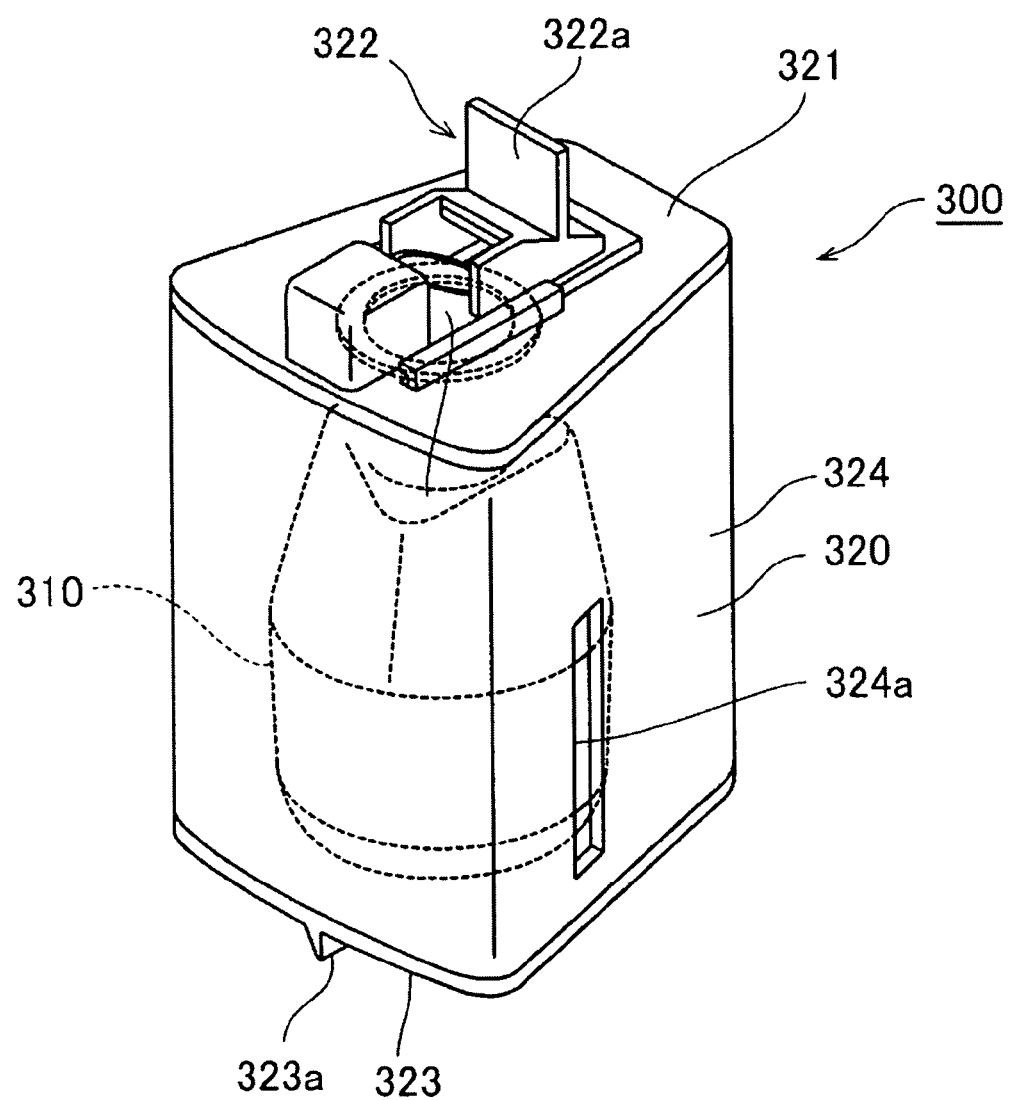
FIG. 17 is an outer appearance view of the reagent container used in the immunological analyzer shown in FIG. 1.
Figure 18:
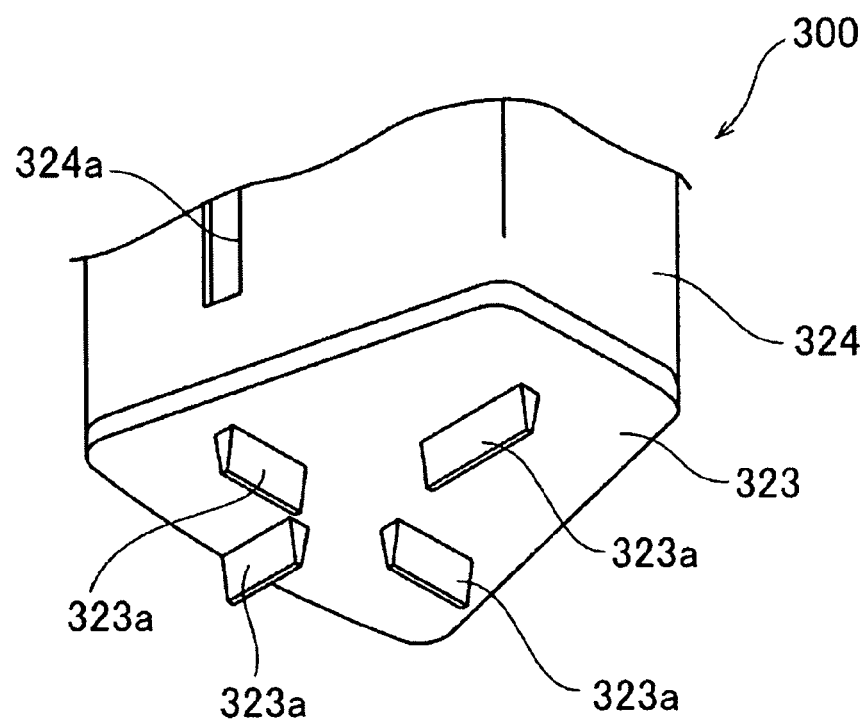
FIG. 18 is a perspective view showing the bottom of the reagent container shown in FIG. 16.
Figure 19:
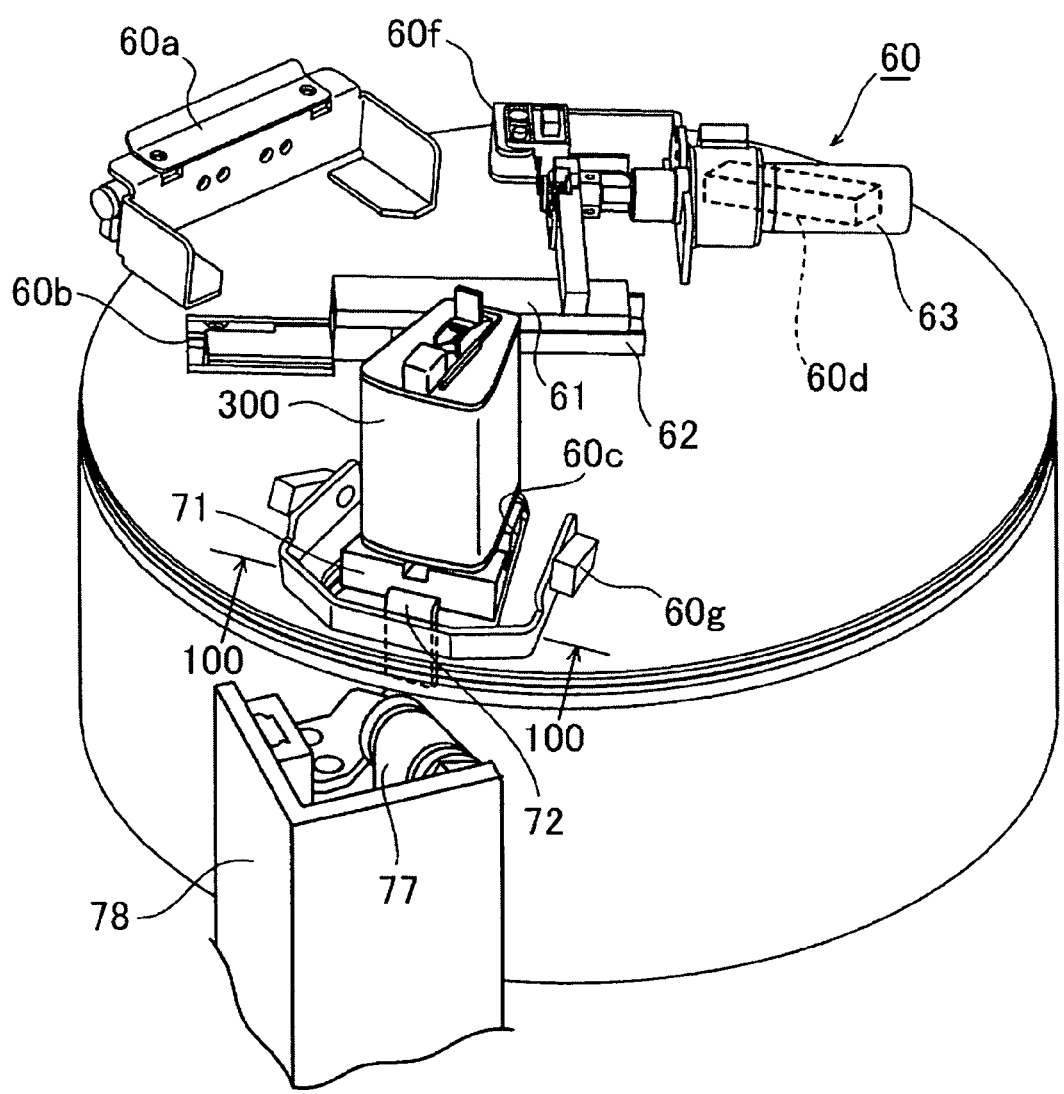
FIG. 19 is a perspective view showing a state in which a mounting platform of the raising and lowering part of the immunological analyzer shown in FIG. 1 is positioned at a mounting/retrieving position.

As shown in FIGS. 16 to 18, the reagent container 300 is made up of a reagent container 310 accommodating the R2 reagent, and a case 320 accommodating the reagent container 310. A slide lid 322 for sealing the reagent container 310 is formed on the upper surface 321 of the case 320. An engagement strip 322a for engaging the two-forked engagement strip 61a of the openable/closable member 61 is formed in the slide lid 322. A cross-shaped rib 323a that engages a groove 71a of the mounting platform 71 of the raising and lowering part 70 is arranged in the bottom 323 of the case 320. A slit 324a (see FIG. 17) for visually recognizing the amount of reagent accommodated in the reagent container 310 is formed at the side surface 324 of case 320.

The reagent installing unit 6 comprises a reagent information reading unit (barcode reader) (not shown). This reagent information reading unit reads a barcode provided with a reagent container set in the reagent installing unit 6.

The reagent installing unit 6 has a configuration similar to the reagent installing unit 7 except for that two openable/closable mechanisms are arranged on the lid 30 in correspondence to the reagent container including two reagent containers of R1 reagent and the R3 reagent, and thus the description thereof will be omitted.

Addition, replacement, and retrieval operations of the reagent container 300 in the reagent installing unit 7 of the immunological analyzer 1 according to the present embodiment will now be described with reference to the FIGS. 8, 10, and 19 to 22.

As shown in FIG. 10, the mounting platform 71 is arranged at the mounting/retrieving position (state when the sensor 70a is ON) in the waiting state. When adding the reagent container 300, the user first mounts the reagent container 300 on the mounting platform 71, a shown in FIGS. 19 and 21.

Figure 20:
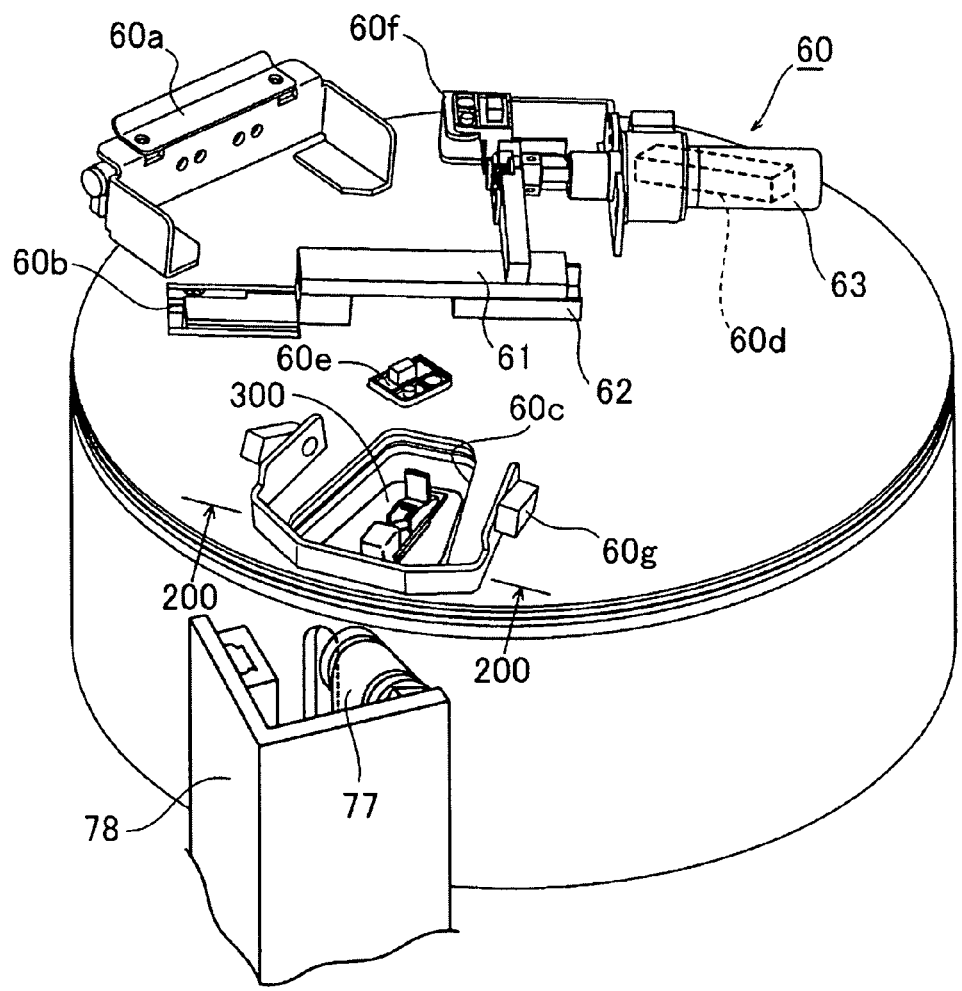
FIG. 20 is a perspective view showing a state in which the mounting platform of the raising and lowering part of the immunological analyzer shown in FIG. 1 is positioned at a bottom dead point.
Figure 21:
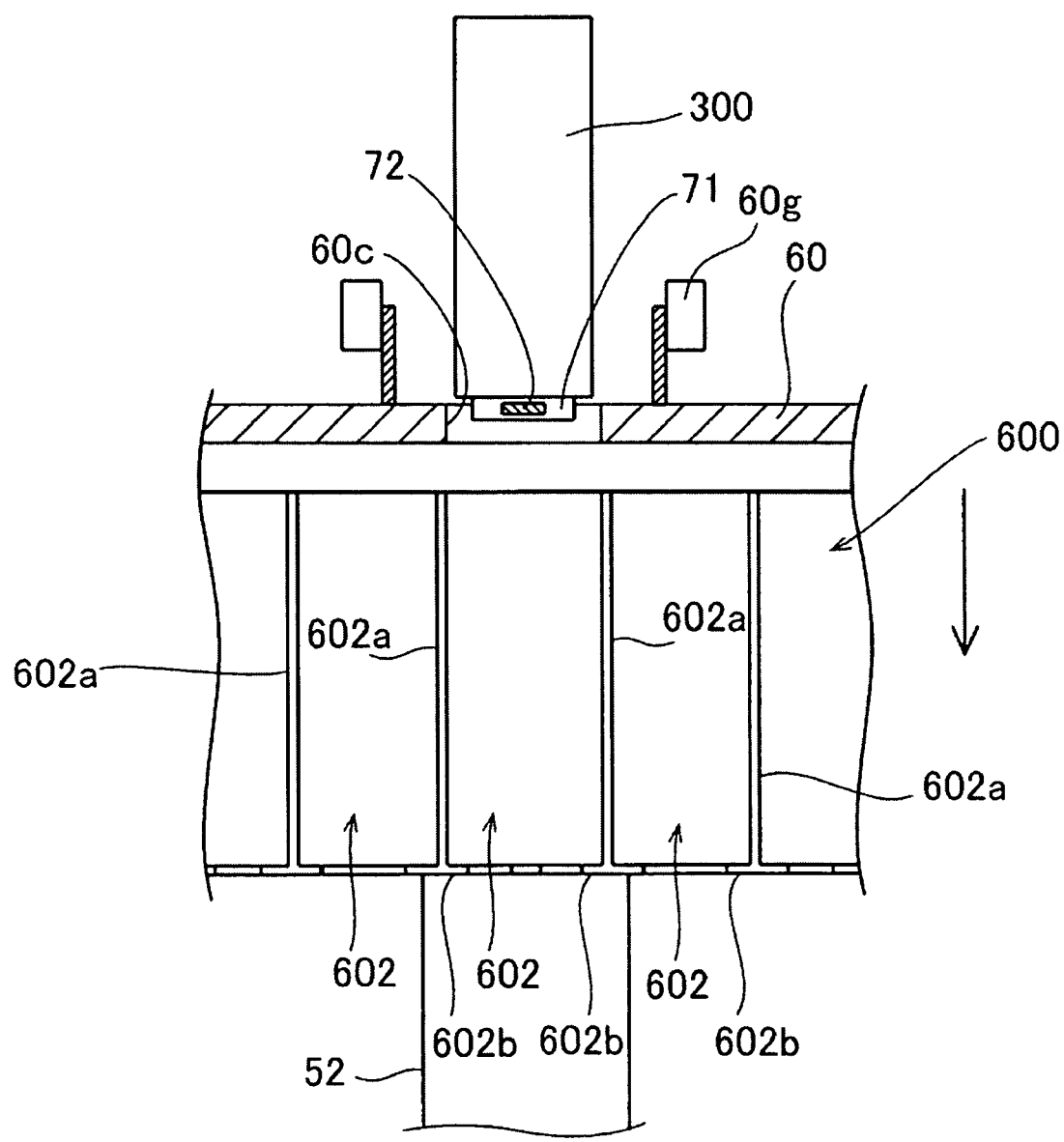
FIG. 21 is a cross sectional view taken along line 100-100 of FIG. 19.
Figure 22:
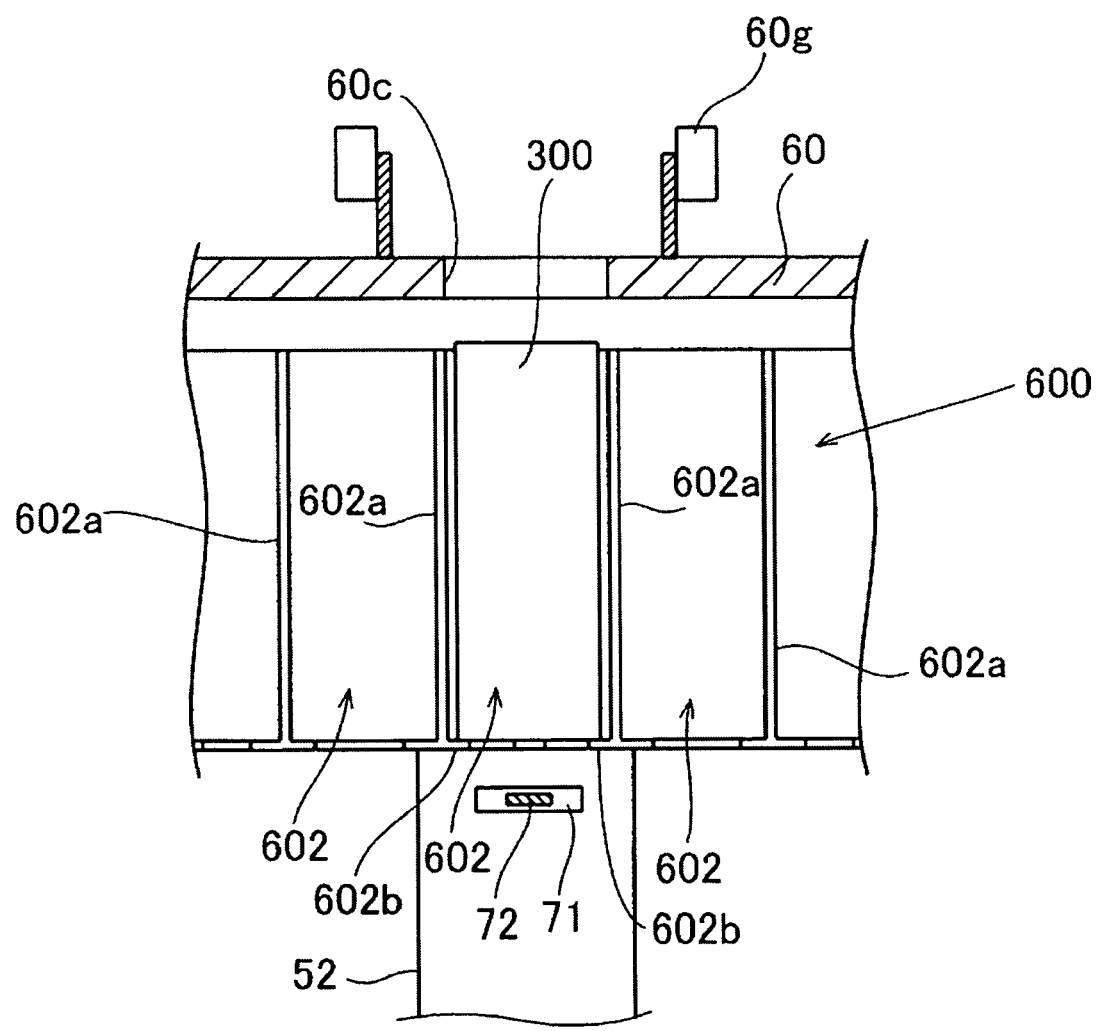
FIG. 22 is a cross sectional view taken along line 200-200 of FIG. 20.

The addition of the reagent container 300 starts when the user instructs the addition of reagent by the control device 4. When the addition of the reagent container 300 starts, the rack 600 is rotated by the drive of the stepping motor 53 (see FIG. 8), and the holder 602 not holding the reagent container 300 is moved to below the input/output hole 60c of the lid 60. Subsequently, the movement to below the mounting platform 71 starts by the drive of the motor 76, as shown in FIG. 20. As shown in FIG. 22, when the mounting platform 71 passes through the supporting part 602b of the holder 602, the peripheral edge of the bottom 323 of the reagent container 300 is supported by the supporting part 602b and the reagent container 300 is held by the holder 602.

When the detection strip 73b is detected by the sensor 70b, the drive of the motor 76 is stopped. The rack 600 is rotated in this state by the drive of the stepping motor 53, and the holder 602 not holding the reagent container 300 is moved to a waiting position below (above the mounting platform 71 at the bottom dead point) of the input/output hole 60c. The movement to above the mounting platform 71 then starts by the drive of the motor 76. The mounting platform 71 passes through the holder 602 not holding the reagent container 300. The mounting platform 71 is then raised until the sensor 70a detects the detection strip 73b, and is arranged at the mounting/retrieving position. The addition of the reagent container 300 is performed in such manner in the present embodiment.

When replacing the reagent container 300, the user mounts the reagent container 300 on the mounting platform 71 at the mounting/retrieving position, and then makes an instruction for replacement by the control device 4. The mounting platform 71 thereby lowers, the reagent container 300 is held in the rack 600, and the mounting platform 71 moves to the bottom dead point (state when the sensor 70*b* is ON).

Thereafter, the rack 600 is rotated by the drive of the stepping motor 53, and the holder 602 holding the reagent container 300 to be replaced is moved to below the input/output hole 60*c* (above the mounting platform 71 at the bottom dead point). The movement to above the mounting platform 71 then starts by the drive of the motor 76. The mounting platform 71 that is being raised lifts the reagent container 300 supported by the supporting part 602*b* of the holder 602, and further rises. The mounting platform 71 is raised until the sensor 70*a* detects the detection strip 73*b*, and is then arranged at the mounting/retrieving position. The reagent container 300 to be replaced is thereby retrieved to the outside of the reagent installing unit 7. The replacement of the reagent container 300 is performed in this manner in the present embodiment.

When retrieving the reagent container 300, instruction for retrieval is made by the control device 4. First, the rack 600 is rotated by the drive of the stepping motor 53, and the holder 602 not holding the reagent container 300 is moved to below the input/output hole 60*c* (above the mounting platform 71 at the bottom dead point). The mounting platform 71 then passes through the holder 602 not holding the reagent container 300 and moved to the bottom dead point (state when the sensor 70*b* is ON). The rack 600 is then rotated, and the holder 602 holding the reagent container 300 to be retrieved is moved to above the mounting platform 602. Thereafter, the mounting platform 71 is raised, and the reagent container 300 to be retrieved is retrieved to the outside of the reagent installing unit 7.

The replacement, addition, and retrieval of the reagent container in the reagent installing unit 6 are also performed similar to the reagent container 300 in the reagent installing unit 7, and thus the description will be omitted.

The aspirating operation of aspirating the reagent from the reagent container 300 by the pipette 9*e* of the reagent dispensing arm 9 according to the present embodiment will now be described with reference to FIGS. 1, 8, 11, 23, and 24.

Figure 23:
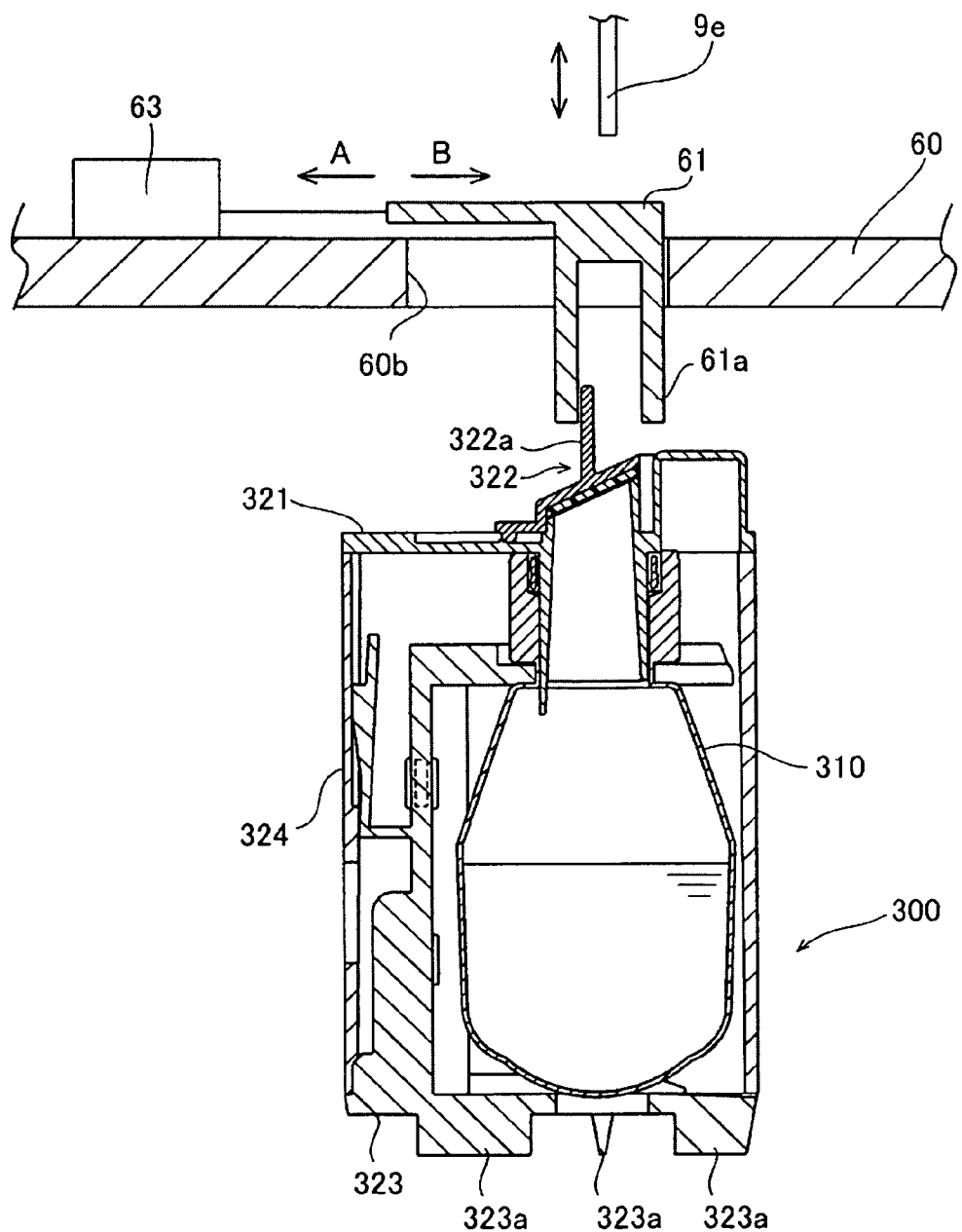
FIG. 23 is a cross sectional view showing a state in which a slide lid of the reagent container is closed upon aspirating the reagent.

The reagent container 300 including the reagent container 310 accommodating the reagent to be aspirated is moved to below the hole 60*b* of the lid 60 by rotating the rack 600 in which the rotation shaft 52 (see FIG. 8) of the reagent holder 50 holds the reagent container 300. The engagement strip 322*a* of the slide lid 322 is arranged between the two-forked engagement strip 61*a* of the openable/closable member 61 of the lid 60, as shown in FIG. 23, if the slide lid 322 of the reagent container 300 is closed when the reagent container 300 is moved to below the hole 60*b* of the lid 60. The engagement strip 322*a* of the slide lid 322 is guided by the guide strip 60*h* (see FIG. 11) arranged near the hole 60*b* of the lid 60 and arranged between the two-forked engagement strip 61*a* of the openable/closable member 61 if the slide lid 322 of the reagent container 300 is opened when the reagent container 300 is moved to below the hole 60*b* of the lid 60.

Figure 24:
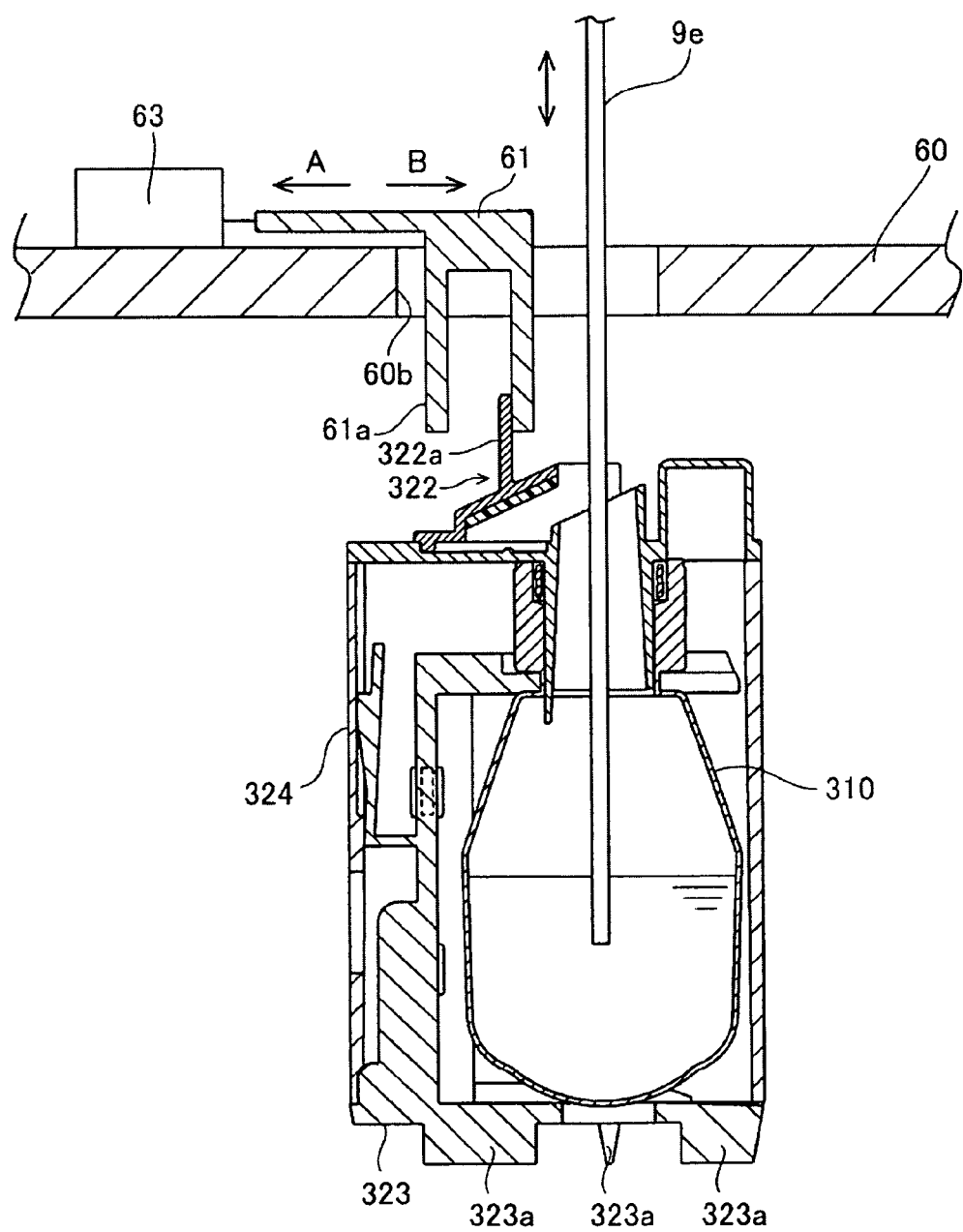
FIG. 24 is a cross sectional view showing a state in which the slide lid of the reagent container is opened upon aspirating the reagent.

If the openable/closable member 61 is slid in the direction of the arrow A by the stepping motor 63 in this state, the engagement strip 322*a* of the slide lid 322 is slid in a direction of the arrow A with the two-forked engagement strip 61*a* so that the slide lid 322 is in an opened state, as shown in FIG. 24. The pipette 9*e* of the reagent dispensing arm 9 then can be inserted into the reagent container 310. The pipette 9*e* is moved to above the hole 60*b* of the lid 60 with turning by the motor 9*a* and the drive transmitting part 9*b*, and the pipette 9*e* is lowered in the opened state of the slide lid 322 so that the pipette 9*e* can be inserted into the reagent container 310 through the hole 60*b* to aspirate the reagent.

The pipette 9*e* that has aspirated the reagent is raised and turned by the motor 9*a* and the drive transmitting part 9*b*, and moved to above the primary reaction unit 11 (see FIG. 1). The reagent aspirated from the reagent container 310 is then dispensed into the cuvette 150 of the primary reaction unit 11.

After the aspirating of the reagent is terminated, the turning member 61 is moved in a direction of the arrow B by the stepping motor 63, whereby the engagement strip 322*a* of the slide lid 322 is slid in the direction of the arrow B with the two-forked engagement strip 61*a*. The slide lid 322 is then closed, and the reagent is in the sealed state. The sealed state of the reagent is thus maintained even when the rack 600 is rotated and the reagent container 300 is moved.

In the present embodiment, the mounting platform 71 is lowered with the reagent container 300 mounted on the mounting platform 71 at the mounting/retrieving position (state when the sensor 70*a* is ON) to hold the reagent container 300 in the holder 602 of the rack 600. The holder 602 of the rack 600 holding the reagent container 300 is arranged above the mounting platform 71 at the bottom dead point (state when the sensor 70*b* is ON) and the mounting platform 71 is raised to lift the reagent container 300 and retrieve the reagent container 300 to the outside of the reagent installing unit 7. According to such configuration, the immunological analyzer 1 can be simplified and miniaturized. The user can mount and retrieve the reagent container 300 to the mounting platform 71 at the mounting/retrieving position, and thus does not need to insert his/her hand into the reagent installing unit 7 when replacing the reagent container 300. The reagent thus can be easily replaced.

Overall Process

Figure 25:
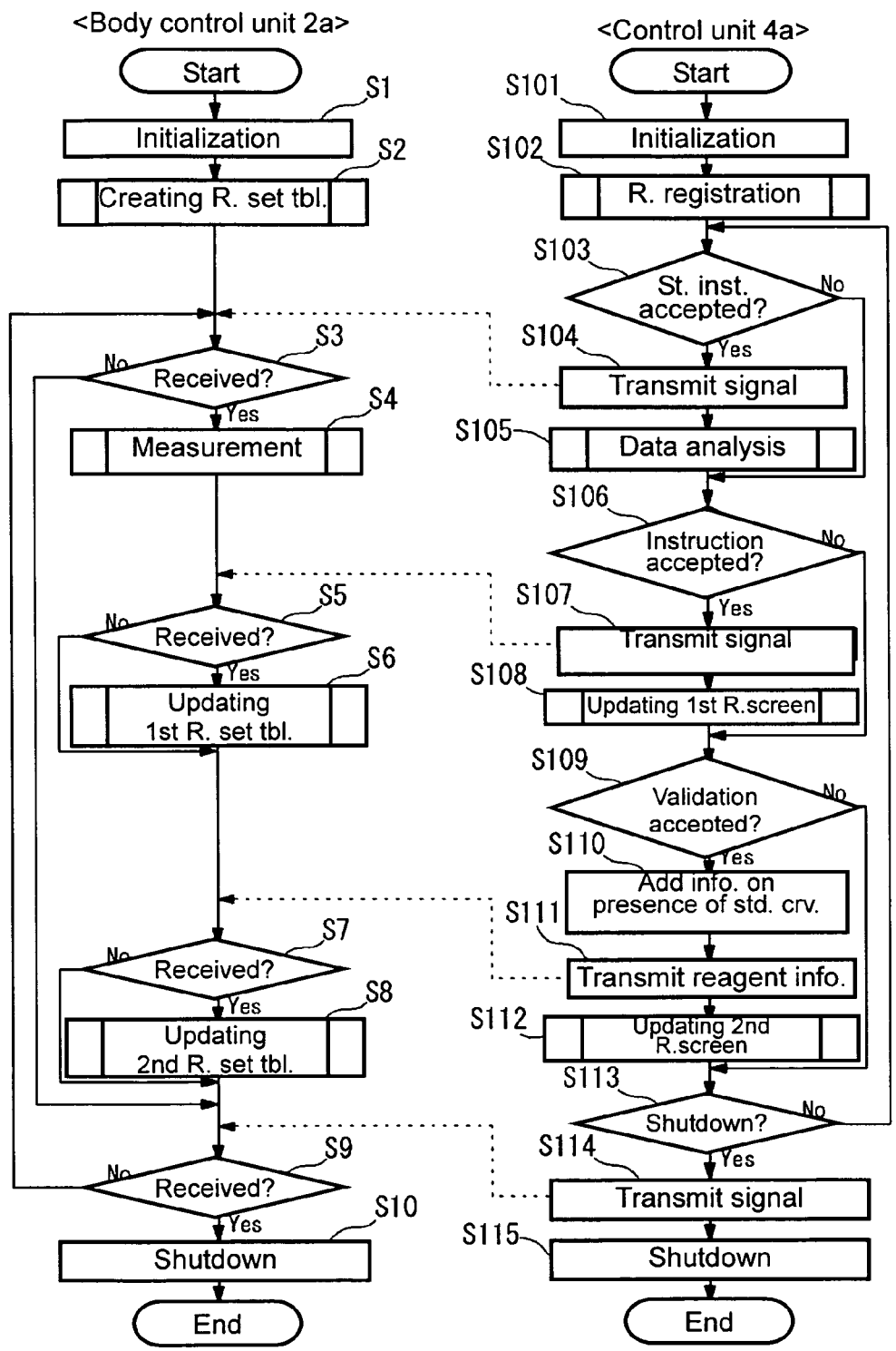
FIG. 25 is a view showing an overall flow of an immunological analysis using the immunological analyzer shown in FIG. 1.

The overall flow of the analyzing process by the immunological analyzer 1 is shown in FIG. 25. If "Yes" and "No" is not described in the determination of the flowchart, downward direction refers to Yes and right (left) refers to No. The process described below is the process controlled by the control unit 4*a* and the body control unit 2*a*.

First, when the power of the immunological analyzer 1 is turned ON, initialization of the body control unit 2*a* is performed (step S1). In the initialization operation, initialization of the program and returning to the origin position of the driving portion of the immunological analyzer 1 are performed.

When the power of the personal computer 401 communicably connected to the immunological analyzer 1 is turned ON, initialization of the control unit 4*a* of the personal computer 401 is performed (step S101). In the initialization operation, initialization of the program etc. is performed. After initialization is completed, registration process of the reagent used in performing analysis using the immunological analyzer 1 is performed (step S102). The reagent registration process is a process of determining usable reagent and determining the usage order of the reagents of the same type with reagent information including information created based on the barcode information arranged on the reagent container 300 and positional information of the reagent container 300 in the reagent installing units 6, and 7, as well as information on the presence/absence of standard curve for the reagent.

The reagent information refers to the information related to the reagent holder 50 of the immunological analyzer 1, and includes, for example, reagent ID (number indicating set position in the reagent holder 50), item (analyzing item) analyzed using the reagent, lot number, serial number, expiration date, remaining quantity, type of reagent (R1 /R3 reagent or R2 reagent), and in the case of measurable reagent set, serial number and information on presence/absence of standard curve of the reagent (R2 reagent in the case of R1/R3 reagent, and R1/R3 reagent in the case of R2 reagent) to be the pairing reagent in the combination configuring the set. The R1/R3 reagent and the R2 reagent are used as a set, but cannot be used as a set when the analyzing items differ or when the lot numbers differ. In the present specification, "measurable reagent set" refers to a set of R1/R3 reagent and R2 reagent that can be used for measurement since the analyzing items are the same and the lot numbers are the same.

After the initialization of the immunological analyzer 1 is completed, the process of creating a reagent set table is performed by the body control unit 2a in step S2. The reagent set table is a table of information related to the reagent, and includes reagent ID, analyzing item, lot number, serial number, expiration date, remaining quantity, type of reagent, and in the case of measurable reagent set, serial number, information on presence/absence of standard curve, and barcode information (image information of the barcode arranged on the reagent container) of the pairing reagent for each reagent. The reagent set table is stored in the RAM 2d of the body control unit 2a after being created. The body control unit 2a holds only reagent ID and the image information of the barcode at the point of reading the barcode of the reagent. The barcode information is transmitted to the control unit 4a to request for other information (reagent information), whereby the control unit 4a acquires the reagent information from the hard disc 401d in response to such request, and transmits the reagent information to the body control unit 2a. The body control unit 2a then acquires various information configuring the reagent set table.

In step S103, the control unit 4a determines whether or not instruction to start the measurement is made. The control unit 4a advances the process to step S104 when determining that instruction to start the measurement is made (Yes), and advances the process to step S106 when determining that instruction to start the measurement is not made (No). In step S104, the control unit 4a transmits a measurement start signal to the body control unit 2a.

In step S3, the body control unit 2a determines whether or not the measurement start signal is received. The body control unit 2a advances the process to step S4 when determining that the measurement start signal is received (Yes), and advances the process to step S9 when determining that the measurement start signal is not received (No).

In step S4, the process of measuring the measurement specimen in which the reagent and the sample are mixed, and obtaining the measurement data is performed.

In step S105, the control unit 4a displays the analysis of the result measured based on the standard curve and the display of the analysis result.

In step S106, the control unit 4a determines whether or not instruction to replace or add the reagent is accepted. The control unit 4a advances the process to step S107 when determining that instruction to replace or add the reagent is made (Yes), and advances the process to step S109 when determining that instruction to replace or add the reagent is not made (No). In step S107, the control unit 4a transmits the reagent replacing/adding instruction signal to the body control unit 2a.

In step S5, the body control unit 2a determines whether or not the reagent replacing/adding instruction signal is received. The body control unit 2a advances the process to step S6 when determining that the reagent replacing/adding instruction signal is received (Yes), and advances the process to step S7 when determining that reagent replacing/adding instruction signal is not received (No).

Figure 33:
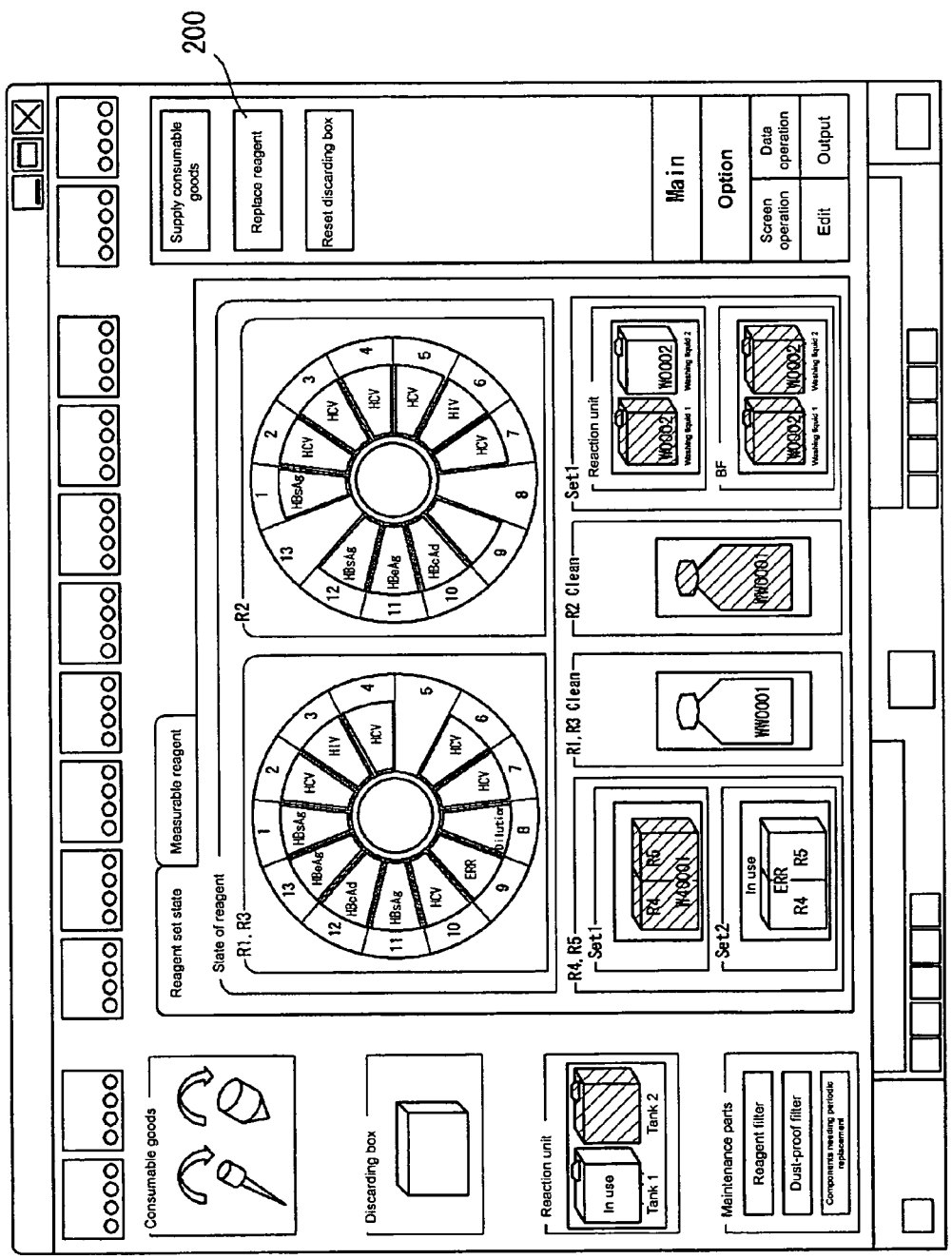
FIG. 33 is an example of a reagent set state screen showing a reagent set state.
Figure 34:
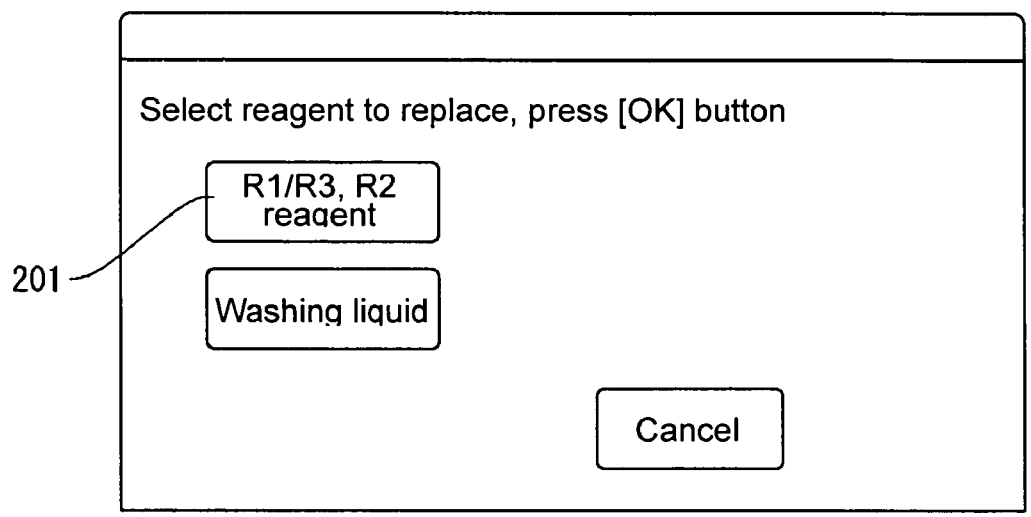
FIG. 34 is an example of a reagent replacement dialogue.

The reagent may be added to an empty set position of the reagent holder or may be replaced with the reagent currently set in the reagent holder. The replacement of the reagent may be set replacement in which the R1/R3 reagent and the R2 reagent are replaced in units of sets or may be individual replacement in which the R1/R3 reagent or the R2 reagent is individually replaced. For instance, when replacing the R1/R3 reagent and the R2 reagent in sets, a "replace reagent" button 200 is selected on a reagent set state screen shown in FIG. 33. A "reagent replacement dialogue" shown in FIG. 34 is then displayed. In the "reagent replacement dialogue", "R1/R3, R2 reagent" button 201 is selected, and "OK" button (not shown) displayed thereafter is pressed, whereby "R1/R3, R2 reagent replacement dialogue" shown in FIG. 35 is displayed. In the "R1/R3, R2 reagent replacement dialogue", the reagent to be replaced is identified. When replacing with a new filled reagent, the filled reagents (R1/R3 reagent and R2 reagent) are mounted on the respective replacement position. When "replace" button 202 is selected after mounting, the filled reagent is first retrieved to the empty set position of the reagent holder, and the reagent to be replaced is discharged from the reagent holder. The reagent to be replaced does not necessarily need to be reagents having the same analyzing items, and may be replaced with the reagent having different analyzing items. When simply retrieving the reagent held in the reagent holder, the reagent to be retrieved is selected in the "R1/R2 reagent, R2 reagent replacement dialogue", and the "retrieve" button 203 is pushed so that the selected reagent is discharged to the replacement position.

In order to respond to a case where the R1/R3 reagent and the R2 reagent not forming a set (same analyzing item) are replaced by mistake, only the R1/R3 reagent or only the R2 reagent may be replaced.

Figure 36:
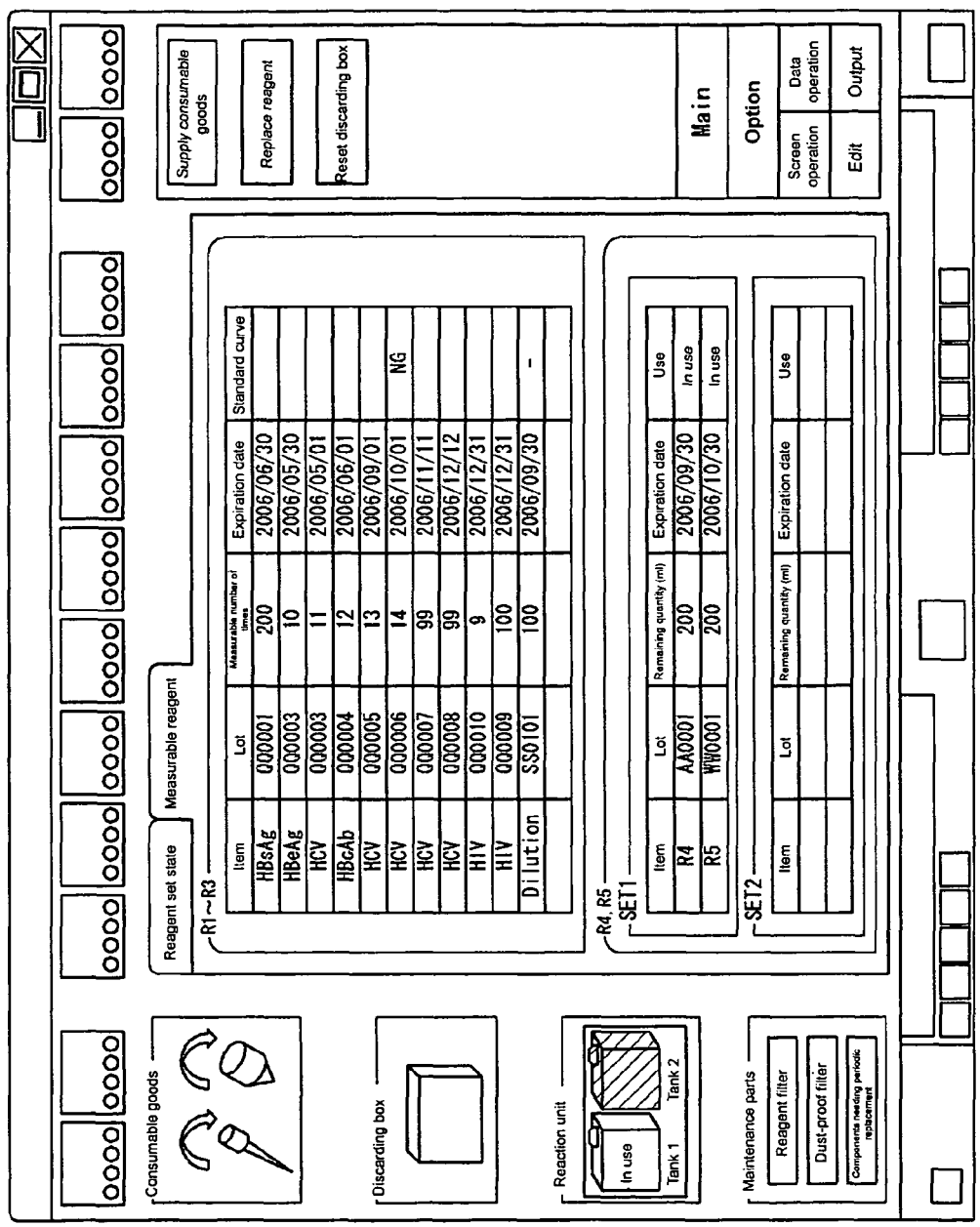
FIG. 36 is an example of a measurable reagent list screen showing measurable reagents in a list.

After the replacement, the barcode information arranged on the newly set reagent container is read by a reagent information reading unit (barcode reader), and transmitted to the control unit 4a as described above. The reagent information corresponding to the barcode information is transmitted from the control unit 4a to the body control unit 2a, and a reagent set state screen (FIG. 33), a R/R3, R2 reagent replacement dialogue screen (FIG. 35), and a measurable reagent screen (FIG. 36) displaying the analyzing items, the lot number etc. of the reagent as a list are updated by the control unit 4a.

In step S6, the body control unit 2a performs the updating process of the first reagent table.

In step S108, the control unit 4a performs the updating process of the first reagent screen.

In step S109, the control unit 4a determines whether or not the validation of the standard curve is accepted. The control unit 4a advances the process to step S110 when determining that the validation of the standard curve is accepted (Yes), and advances the process to step S113 when determining that the validation of the standard curve is not accepted (No). In step S110, the control unit 4a adds information on the presence of the standard curve to the reagent information of the relevant reagent. In step S111, the control unit 4a transmits the reagent information to the body control unit 2a.

The standard curve is created by registering the standard curve measurement order in the order registration screen of the immunological analyzer 1, and measuring the calibrator (with antigen or antibody of known concentration (antigen when analyzing item is antigen, and antibody when analyzing item is antibody). The control unit 4a creates the standard curve by causing the CPU 401a to execute the program installed in the hard disc 401d based on the count value (photon amount data detected by the detector 15) of the measurement data of the calibrator and the concentration of the calibrator. The created standard curve may not be used as it is, or may be used when performing concentration calculation (conversion from measurement data to concentration data) in the subsequent analyzing step through validate operation (standard curve validation) by the user. The standard curve created and validated in such manner is stored in a standard curve database of the hard disc 401*d* in correspondence to the lot number of the reagent used in the measurement of the calibrator. The standard curve stored in this manner is used for the processing of the measurement data when the specimen is measured using the corresponding reagent, that is, the reagent of the corresponding lot number.

In step S7, the body control unit 2*a* determines whether or not the reagent information is received. The body control unit 2*a* advances the process to step S8 when determining that the reagent information is received (Yes), and advances the process to step S9 when determining that the reagent information is not received (No).

In step S8, the body control unit 2*a* performs the updating process of the second reagent table.

In step S112, the control unit 4*a* performs the updating process of the second reagent screen.

In step S113, the control unit 4*a* determines whether or not an instruction to shutdown the personal computer 401 is accepted. The control unit 4*a* advances the process to step S114 when determining that the instruction to shutdown is accepted (Yes), and returns to step S103 when determining that the instruction to shutdown is not accepted (No).

In step S114, the control unit 4*a* transmits a shutdown signal to the body control unit 2*a*.

In step S115, the control unit 4*a* shuts down the personal computer 401 and terminates the process.

In step S9, the body control unit 2*a* determines whether or not the shutdown signal is received. The body control unit 2*a* advances the process to step S110 when determining that the shutdown signal is received (Yes), and returns the process to step S3 when determining that the shutdown signal is not received (No).

In step S10, the body control unit 2*a* shuts down the immunological analyzer 1 and terminates the process.

Reagent Registration Process and Reagent Set Table Creating Process

Figure 26:
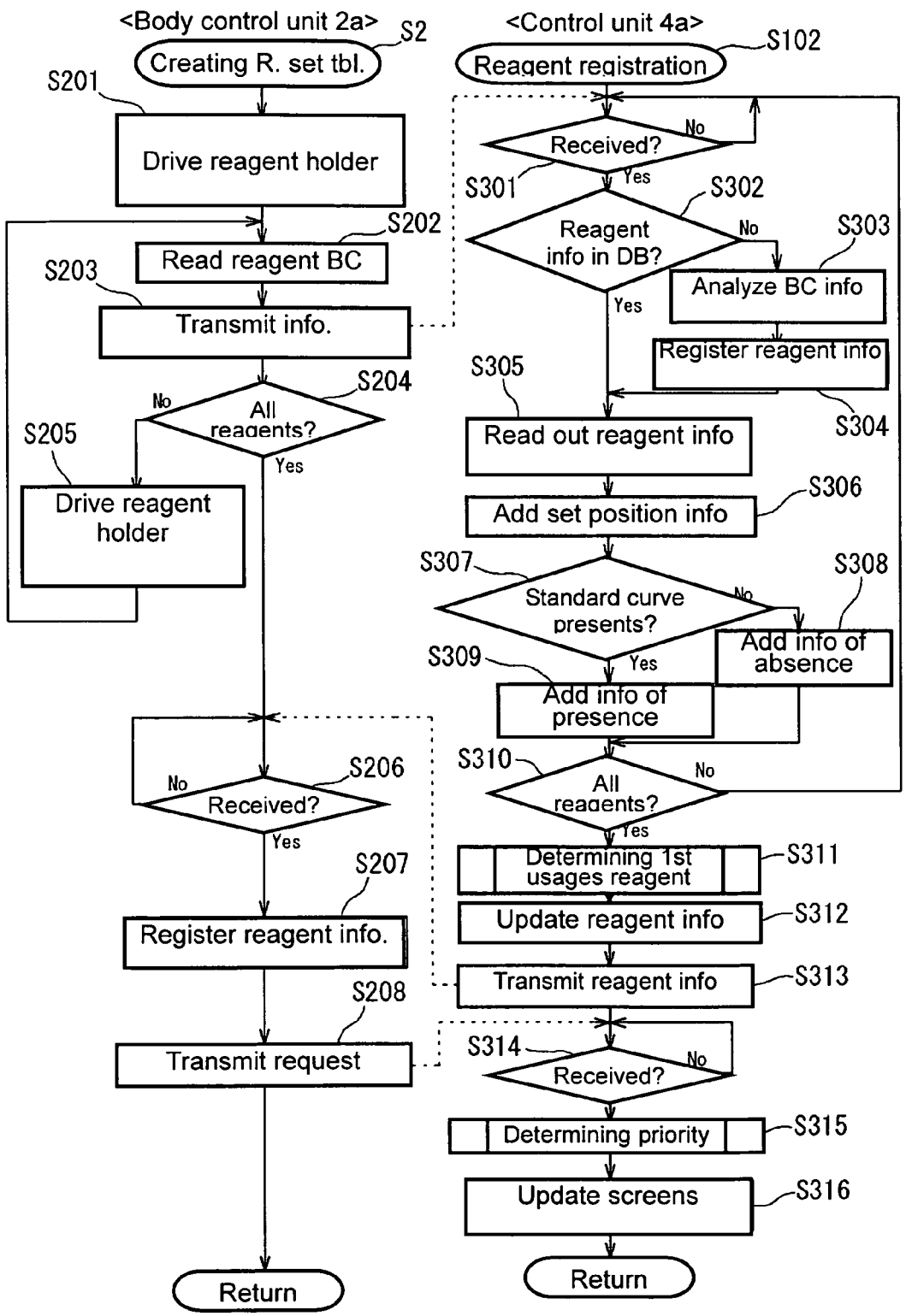
FIG. 26 is a view showing a flow of a reagent registration process and a reagent set table creating process.

The flow of the reagent registration process in step S102 and the reagent set table creating process in step S2 are shown in FIG. 26.

First, in step S201, the reagent holder is driven so that the reagent container at the first set position is positioned at the reagent barcode reading position arranged at the reagent container. A plurality of reagent containers can be installed in the reagent holder, but a number (reagent ID) is set in advance with respect to the plurality of installation (set) positions. In step S201, the reagent container is moved to the reagent barcode reading position to read the reagent barcode of the reagent container which reagent ID is arranged at the position of "1".

In step S202, the reagent barcode of the reagent container is read by the barcode reader arranged at the reagent barcode reading position.

In step S203, information on the set position at where the reagent container performed with reading of the reagent barcode is installed, that is, the reagent ID and the read barcode information are transmitted from the body control unit 2*a* to the control unit 4*a*.

In step S301, the control unit 4*a* determines whether or not the information on the set position and the barcode information are received. The control unit 4*a* advances the process to step S302 when determining that the information on the set position and the barcode information are received (Yes).

In step S302, the control unit 4*a* determines whether or not the reagent information with respect to the received barcode information is stored in a reagent database in the hard disc 401*d*. The control unit 4*a* advances the process to step S305 when determining that the reagent information is stored in the reagent database (Yes), and advances the process to step S303 when determining that the reagent information is not stored in the reagent database (No).

If the reagent information with respect to the received barcode information is not stored in the reagent database in the hard disc 401*d*, the control unit 4*a* analyzes the received barcode information in step S303, and then registers the obtained reagent information in the reagent database in the hard disc 401*d* in step S304.

In step S305, the control unit 4*a* reads out the reagent information corresponding to the barcode information from the reagent database in the hard disc 401*d*. In step S306, the control unit 4*a* adds the set position information transmitted from the body control unit 2*a* to the read reagent information.

In step S307, the control unit 4*a* determines whether or not the standard curve corresponding to the lot number contained in the reagent information is stored in a standard curve database in the hard disc 401*d*. The control unit 4*a* advances the process to step S309 when determining that the standard curve corresponding to the lot number contained in the reagent information is stored in the standard curve database (Yes) and advances the process to step S308 when determining that the standard curve is not stored in the standard curve database (No). In step S308, information of "no standard curve" is added to the reagent information.

In step S310, the control unit 4*a* determines whether or not registration (registration to the reagent database) of the reagent information including the presence/absence of the standard curve is terminated for the reagent of all the reagent containers set in the reagent holder. The control unit 4*a* advances the process to step S311 when determining that registration is terminated for the reagent of all the reagent containers set in the reagent holder (Yes), and returns the process to step S301 when determining that registration is not terminated for the reagent of all the reagent containers set in the reagent holder (No).

In step S204, the body control unit 2*a* determines whether or not transmission of the set position information and the barcode information to the control unit 4*a* is terminated for the reagent of all the reagent containers set in the reagent holder. The body control unit 2*a* advances the process to step S206 when determining that transmission of the information is terminated for the reagent of all the reagent containers set in the reagent holder (Yes), and drives the reagent holder (step S205) so that the reagent container of the next set position is positioned at the reagent barcode reading position and returns the process to step S202 when determining that transmission of the information is not terminated for the reagent of all the reagent containers set in the reagent holder (No).

In step S311, the control unit 4*a* performs a determination process of a first usable reagent described below.

In step S312, the control unit 4*a* performs an updating process of the reagent information stored in the reagent database, and transmits the updated reagent information to the body control unit 2*a* in step S313.

In step S206, the body control unit 2*a* determines whether or not the updated reagent information is received. The body control unit 2*a* advances the process to step S207 when determining that the updated reagent information is received (Yes).

In step S207, the body control unit 2a registers the received reagent information in the RAM 2d.

In step S208, the body control unit 2a transmits a signal requesting for update of the reagent list to the control unit 4a.

In step S314, the control unit 4a determines whether or not the signal requesting for update of the reagent list is received. The control unit 4a advances the process to step S315 when determining that the signal requesting for update of the reagent list is received (Yes).

In step S315, the control unit 4a performs the process of determining the usage order (priority) of the reagent when a plurality of the same types of reagents exists, as described below.

In step S316, the control unit 4a updates the reagent set state screen and the measurable reagent list screen.

Measurement Process and Data Analyzing Process

Figure 27:
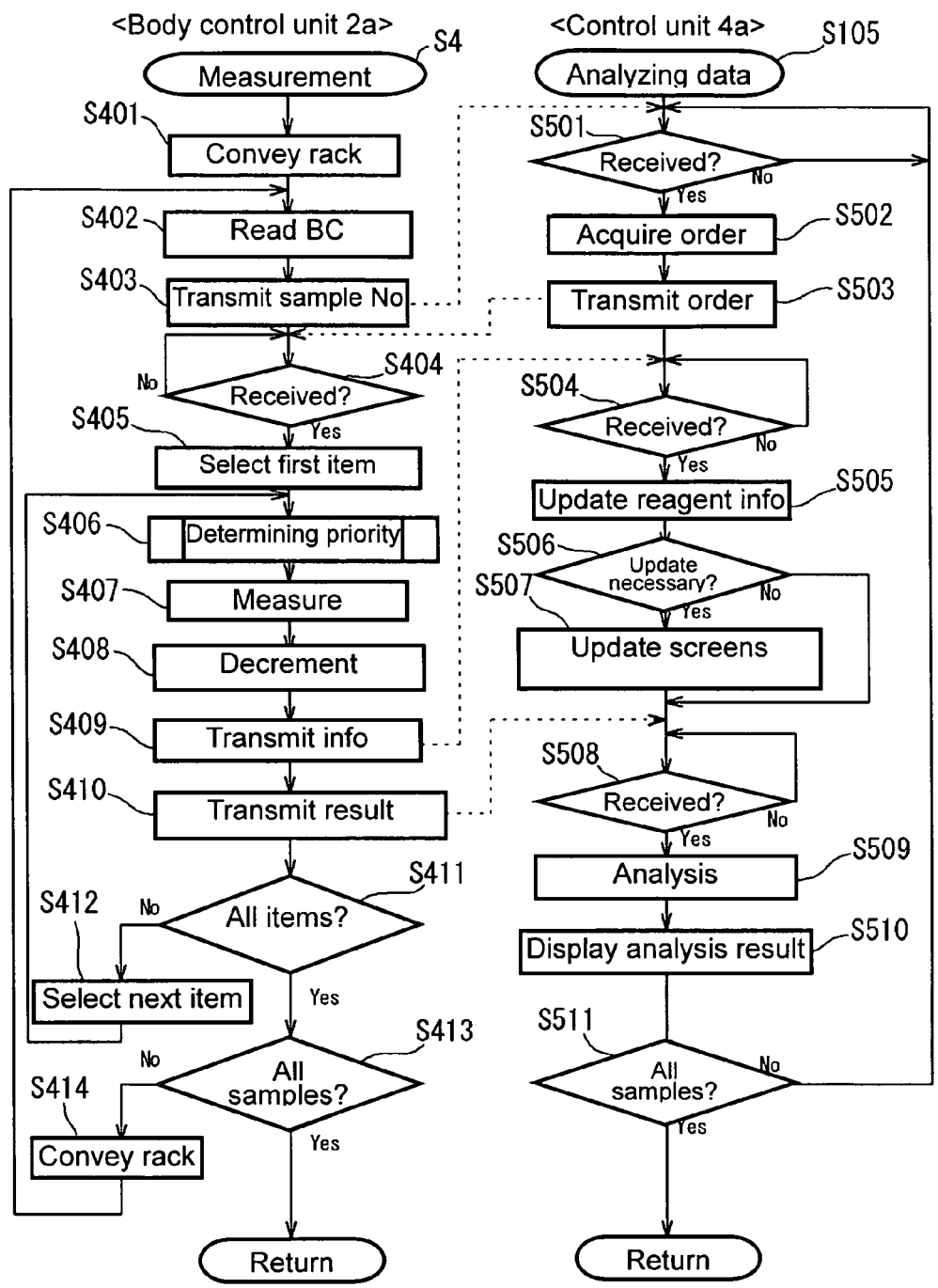
FIG. 27 is a view showing a flow of a measurement process and a data analyzing process.

The flow of the measurement process in step S4 and the data analyzing process in step S105 is shown in FIG. 27.

First, in step S401, the rack 101 mounted with a plurality of test tubes 100 accommodating the sample is conveyed to the position corresponding to the aspirating position 1a of the sample dispensing arm 5 by the sample conveyance section 3. A barcode recorded with information for specifying the test tube 100 is given to each test tube 100 accommodated in the rack 101, and the barcode is read by the barcode reader (not shown) serving as a detection unit arranged on the conveyance path for conveying the test tube 100 to the predetermined position (step S402). The body control unit 2a transmits the read sample number to the control unit 4a in step S403.

In step S501, the control unit 4a determines whether or not the sample number is received. The control unit 4a advances the process to step S502 when determining that the sample number is received (Yes). In step S502, the control unit 4a acquires the order of the sample analysis, and transmits the acquired order to the body control unit 2a in step S503.

In step S404, the body control unit 2a determines whether or not the order of sample analysis is received. The body control unit 2a advances the process to step S405 when determining that the order of sample analysis is received (Yes).

In step S405, the body control unit 2a selects the first measurement item from the plurality of measurement items contained in the order of sample analysis.

In step S406, the body control unit 2a performs determination process of the usage priority when a plurality of the same type of usable reagents exists.

In step S407, measurement is performed on the ordered item.

In step S408, the body control unit 2a decrements the remaining quantity of the reagent used in the measurement of step S407, and thereafter, the body control unit 2a transmits the reagent ID related to the used reagent, that is, the number indicating the set position in the reagent holder of the reagent container accommodating the used reagent and the remaining quantity information of the reagent to the control unit 4a (step S409).

In step S504, the control unit 4a determines whether or not the reagent ID and the remaining quantity information of the reagent are received. The control unit 4a advances the process to step S505 when determining that the reagent ID and the remaining quantity information of the reagent are received (Yes). In step S505, the control unit 4a updates the reagent information in the reagent database. In this case, the usage usability information of the reagent is set to "not usable" when the remaining quantity of the reagent is zero.

In step S506, the control unit 4a determines whether or not the update of the reagent set state screen and the measurable reagent list screen displayed on the display 4b is necessary based on the updated reagent information. In order to prevent measurement error due to lack of reagent, the user is able to recognize the reagent having a remaining quantity of lower than or equal to a predetermined value on the reagent set state screen (see FIG. 33) schematically showing the state the reagent is set in the reagent holder and the screen (see FIG. 36) displaying the measurable reagent in a form of a list in the present embodiment. Specifically, when the remaining quantity becomes lower than or equal to the quantity for a predetermined number of measurements, the color of the region (FIG. 33) or the column (FIG. 36) displaying the reagent is changed from the color of pairing reagents to warn the user that the reagent is running out. In this manner, the reagent without any remaining quantity is not used, and the user is warned when the remaining quantity of the reagent becomes small, whereby the remaining quantity of the reagent can be appropriately managed.

In step S410, the body control unit 2a transmits the measurement data obtained in step S407 to the control unit 4a.

In step S508, the control unit 4a determines whether or not the measurement data is received. The control unit 4a advances the process to step S509 when determining that the measurement data is received (Yes).

In step S509, the control unit 4a performs the analyzing process of the measurement data transmitted from the body control unit 2a side. That is, the control unit 4a calculates the concentration of the antigen to be measured from the transmitted measurement data and the standard curve created using the standard specimen in advance and stored in the standard curve database of the hard disc 401d, and stores the result (analysis result). The control unit 4a outputs the analysis result (step S510).

In step S411, the body control unit 2a determines whether or not the measurement for all the items of the received order is terminated. The body control unit 2a advances the process to step S413 when determining that the measurement for all the items is terminated (Yes), and selects the next item (step S412) and returns the process to step S406 when determining that the measurement for all the items is not terminated (No).

In step S413, the body control unit 2a determines whether or not the measurement is performed for the sample in all the test tubes 100 held by the rack 101. The body control unit 2a advances the process to step S5 when determining that the measurement for the sample in all the test tubes 100 held by the rack 101 is performed (Yes), and conveys the rack 101 by a predetermined distance (distance for the test tube accommodating the sample to be measured next to reach the aspirating position) (step S414) and returns the process to step S402 when determining that the measurement for the sample in all the test tubes 100 held by the rack 101 is not performed (No).

In step S511, the control unit 4a determines whether or not the measurement is performed for the sample in all test tubes 100 held by the rack 101. The control unit 4a advances the process to step S106 when determining that the measurement for the sample in all the test tubes 100 held by the rack 101 is performed (Yes), and returns the process to step S501 when determining that the measurement for the sample in all the test tubes 100 held by the rack 101 is not performed (No).

Figure 28:
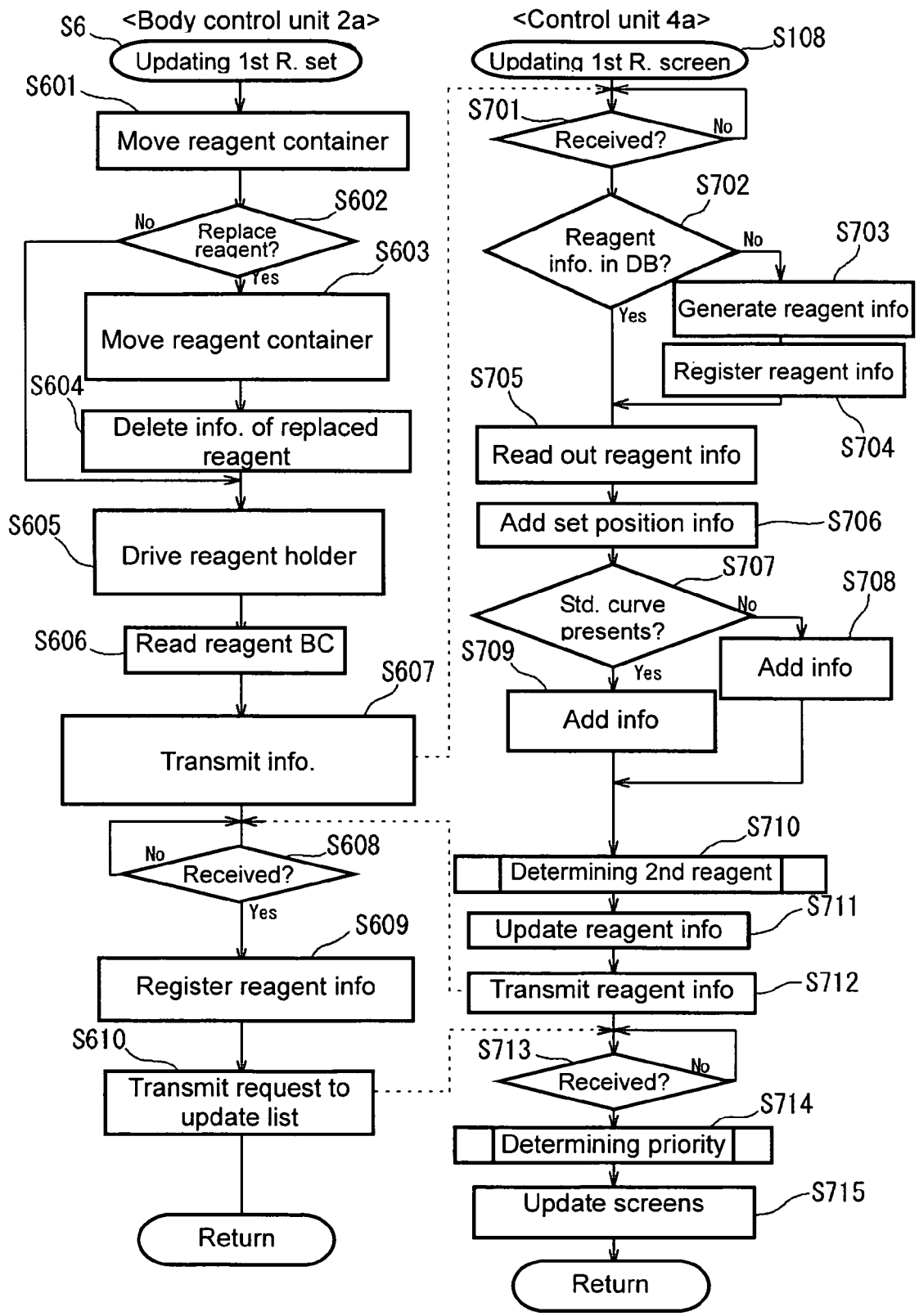
FIG. 28 is a view showing a flow of a first reagent set table updating process and a first reagent screen updating process.

First Reagent Set Table Updating Process and First Reagent Screen Updating Process The flow of the first reagent set table updating process in step S6 and the first reagent screen updating process in step S108 are shown in FIG. 28.

First, in step S601, the raising and lowering part and the reagent holder of the reagent installation unit are driven to move the reagent container (new) to an empty set position of the reagent holder as described above.

In step S602, the body control unit 2a determines whether or not reagent replacement is instructed by the user. The body control unit 2a advances the process to step S603 when determining that reagent replacement is instructed (Yes), and advances the process to step S605 when determining that reagent replacement is not instructed, that is, reagent is to be added (No).

When reagent replacement is instructed, in step S603, the raising and lowering part and the reagent holder of the reagent installation unit are driven to move the reagent container to be replaced from the set position to the retrieving position. In step S604, the body control unit 2a deletes the reagent information regarding the reagent in the reagent container to be replaced from the reagent set table.

In step S605, the reagent holder is driven so that the newly set reagent container is positioned at the reagent barcode reading position.

In step S606, the reagent barcode of the reagent container is read by the barcode reader arranged at the reagent barcode reading position. The body control unit 2a transmits the read barcode information and the set position information (reagent ID) of the newly set reagent container to the control unit 4a in step S607. In the case of reagent replacement, the set position information of the retrieved reagent container is also transmitted.

In step S701, the control unit 4a determines whether or not the barcode information, the set position information of the newly set reagent container, and the set position information of the retrieved reagent container in the case of reagent replacement are received. The control unit 4a advances the process to step S702 when determining that each of information is received (Yes).

In step S702, the control unit 4a determines whether or not the reagent information with respect to the received barcode information is stored in the reagent database in the hard disc 401d. The control unit 4a advances the process to step S705 when determining that the reagent information is stored in the reagent database (Yes), and advances the process to step S703 when determining that the reagent information is not stored in the reagent database (No).

If the reagent information with respect to the received barcode information is not stored in the reagent database in the hard disc 401d, the control unit 4a analyzes the received barcode information in step S703, and registers the obtained reagent information in the reagent database in the hard disc 401d in step S704. In step S705, the control unit 4a reads out the reagent information with respect to the barcode information from the reagent database in the hard disc 401d. In step S706, the control unit 4a adds the set position information transmitted from the body control unit 2a to the read reagent information.

In step S707, the control unit 4a determines whether or not the standard curve corresponding to the lot number contained in the reagent information is stored in a standard curve database in the hard disc 401d. The control unit 4a advances the process to step S709 when determining that the standard curve corresponding to the lot number contained in the reagent information is stored in the standard curve database (Yes) and advances the process to step S708 when determining that the standard curve is not stored in the standard curve database (No). In step S708, information of "no standard curve" is added to the reagent information.

In step S710, the control unit 4a performs a determination process of a second usable reagent.

In step S711, the control unit 4a performs the updating process of the reagent information stored in the reagent database, and transmits the updated reagent information to the body control unit 2a in step S712.

In step S608, the body control unit 2a determines whether or not the updated reagent information is received. The body control unit 2a advances the process to step S609 when determining that the updated reagent information is received (Yes). In step S609, the body control unit 2a registers the received reagent information in the RAM 2d.

In step S610, the body control unit 2a transmits a signal requesting for update of the reagent list to the control unit 4a.

In step S713, the control unit 4a determines whether or not the signal requesting for update of the reagent list is received. The control unit 4a advances the process to step S714 when determining that the signal requesting for update of the reagent list is received (Yes).

In step S714, the control unit 4a performs the process of determining the usage order (priority) of the reagent when a plurality of the same types of reagents exists, as described below.

In step S715, the control unit 4a updates the reagent set state screen and the measurable reagent list screen.

Figure 29:
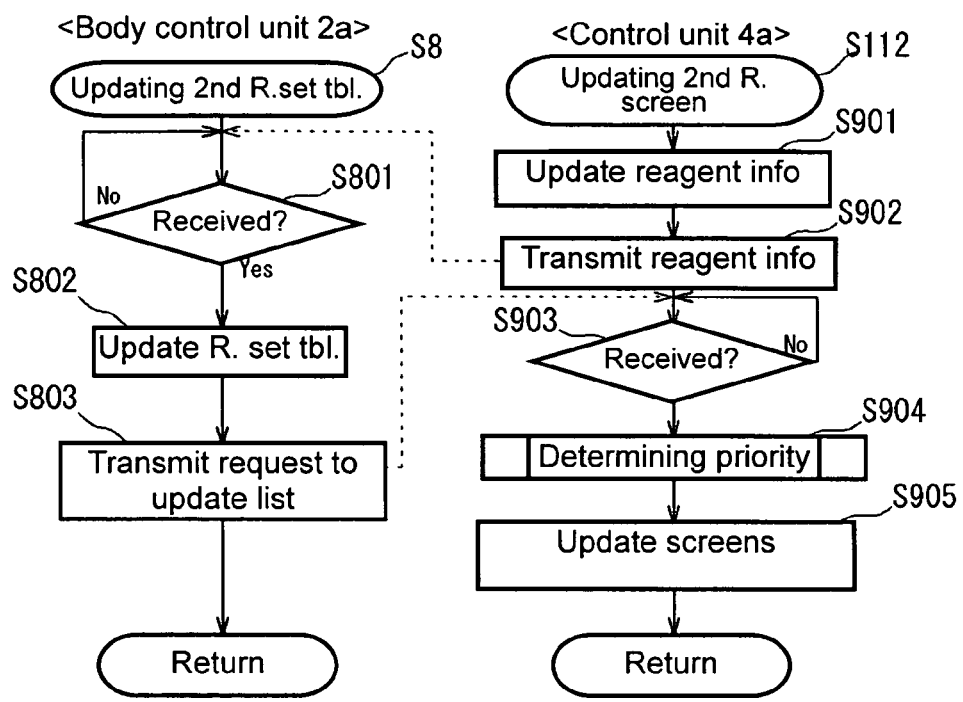
FIG. 29 is a view showing a flow of a second reagent set table updating process and a second reagent screen updating process.

Second Reagent Set Table Updating Process and Second Reagent Screen Updating Process The flow of the second reagent set table updating process in step S8 and the second reagent screen updating process in step S112 is shown in FIG. 29.

First, in step S901, the control unit 4a updates the reagent information and transmits the updated reagent information to the body control unit 2a in step S902.

In step S801, the body control unit 2a determines whether or not the updated reagent information is received.

The body control unit 2a advances the process to step S802 when determining that the updated reagent information is received (Yes). In step S802, the body control unit 2a updates the reagent set table based on the received reagent information.

In step S803, the body control unit 2a transmits the signal requesting for update of the reagent list to the control unit 4a.

In step S903, the control unit 4a determines whether or not the signal requesting for update of the reagent list is received. The control unit 4a advances the process to step S904 when determining that the signal requesting for update of the reagent list is received (Yes).

In step S904, the control unit 4a performs the process of determining the usage order (priority) of the reagent when a plurality of the same types of reagents exists, as described below.

In step S905, the control unit 4a updates the reagent set state screen and the measurable reagent list screen.

First Usable Reagent Determining Process

Figure 30:
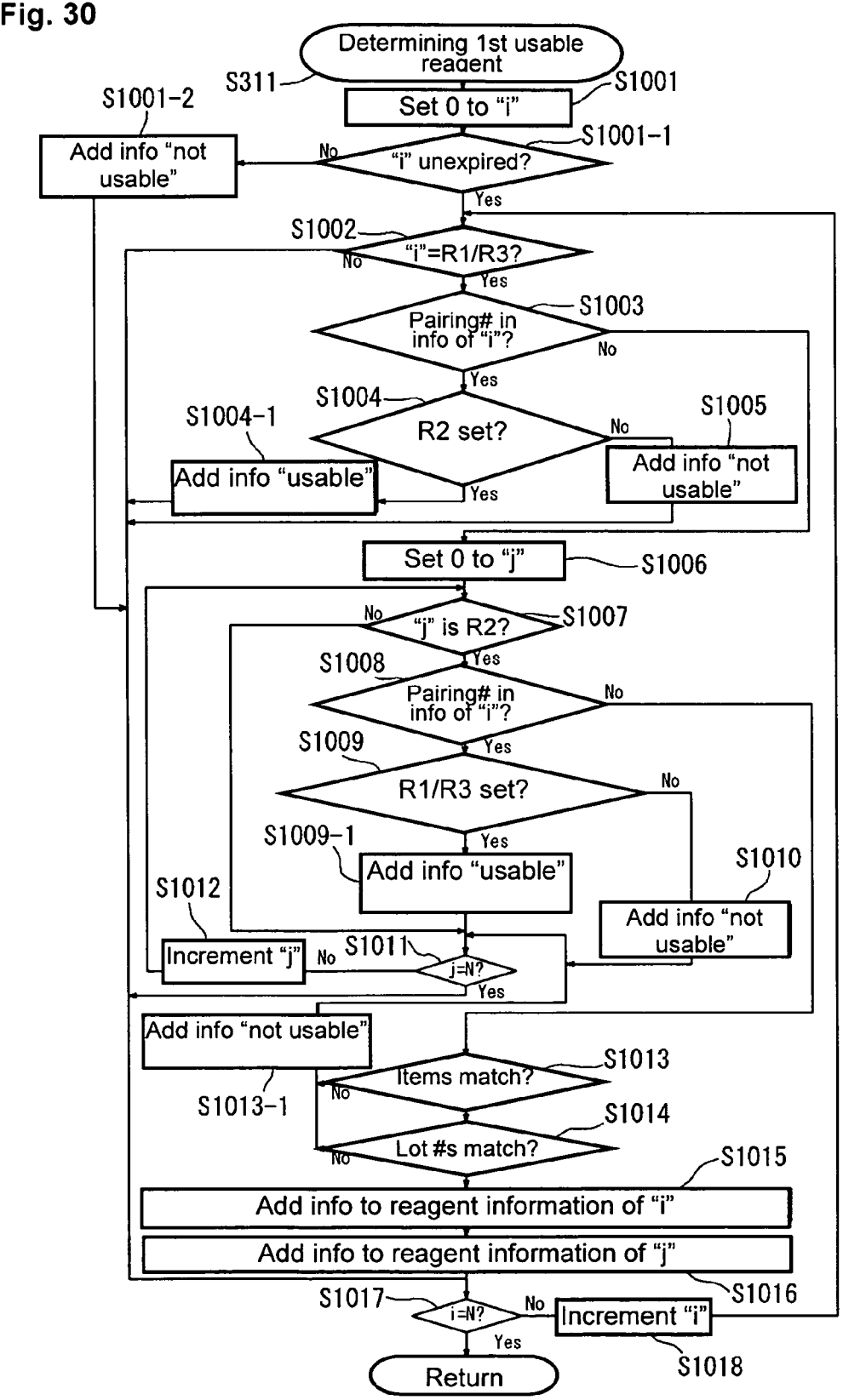
FIG. 30 is a view showing a flow of a first usable reagent determining process.

The flow of the first usable reagent determining process in step S311 is shown in FIG. 30. In the flowchart shown in FIG. 30, "i" and "j" indicate the number (reagent ID) of the reagent set position, and "N" indicates the maximum number of reagent sets, that is, the maximum value of the reagent ID. In the present embodiment, at least one of the plurality of reagent set positions in the reagent holder must always be an empty space, and thus the maximum number of reagent set is a value one less than the number of set position of the reagent container.

In the first usable reagent determining process, determination is made on whether or not all the reagents set in the reagent holder are usable. In the second usable reagent determining process, on the other hand, the flowchart thereof is omitted but determination is made on whether or not only the reagent newly set to the reagent holder through replacement or addition of the reagent is usable through a process similar to the first usable reagent determining process. For instance, when the reagent information of the newly added R1/R3 reagent exists in the reagent database, if a serial number of the reagent to be the pairing reagent configuring the measurable reagent set is included in the reagent information, determination is made on whether or not the R2 reagent identified by the serial number is set in the reagent holder. If the opposing R2 reagent is not set, determination is made whether any of the other currently set R reagents has the same analyzing item and the lot number, and the corresponding R2 reagent, if any, is registered as the usable reagent.

First, in step S1001, the control unit 4a sets "0" to "i". In step S1001-1, the control unit 4a determines whether or not within the expiration date from the expiration date information of the reagent information of "i". If within the expiration date (Yes), the process advances to step S1002. If determined that the expiration date is expired in step S1001-1, the control unit 4a sets "not usable" to the usage usability information of the reagent information of "i" in step S1001-2 and advances the process to step S1017. Thus, the expired reagent is not used, and the expiration date of the reagent is appropriately managed.

In step S1002, the control unit 4a determines whether or not "i" is the R1/R3 reagent. The control unit 4a advances the process to step S1003 when determining that "i" is the R1/R3 reagent (Yes), and advances the process to step S1017 when determining that "i" is not R1/R3 reagent (No).

In step S1003, the control unit 4a determines whether or not a serial number of the reagent (R2 reagent) to be the pairing reagent configuring the measurable reagent set exists in the reagent information of "i". The control unit 4a advances the process to step S1004 when determining that the serial number of the reagent (R2 reagent) to be the pairing reagent exists in the reagent information of "i" (Yes), and advances the process to step S1017 when determining that the serial number of the reagent (R2 reagent) to be the pairing reagent does not exist in the reagent information of "i" (No).

In step S1004, the control unit 4a determines whether or not the R2 reagent identified by the serial number of the reagent to be the pairing reagent is set in the reagent holder. The control unit 4a advances the process to step S1004-1 when determining that the R2 reagent identified by the serial number of the reagent to be the pairing reagent is set in the reagent holder (Yes), adds the information of "usable" to the reagent information of "i" and advances the process to step S1017. The control unit 4a advances the process to step S1005 when determining that the R2 reagent identified by the serial number of the reagent to be the pairing reagent is not set in the reagent holder (No), and adds the information of "not usable" to the reagent information of "i" in step S1005.

In step S1006, "0" is set to "j". In step S1007, the control unit 4a determines whether or not "j" is the R2 reagent. The control unit 4a advances the process to step S1008 when determining that "j" is R2 reagent (Yes), and advances the process to step S1011 when determining that "j" is not R2 reagent (No).

In step S1008, the control unit 4a determines whether or not a serial number of the reagent (R1/R3 reagent) to be the pairing reagent configuring the measurable reagent set exists in the reagent information of "j". The control unit 4a advances the process to step S1009 when determining that the serial number of the reagent (R1/R3 reagent) to be the pairing reagent exists in the reagent information of "j" (Yes), and advances the process to step S1013 when determining that the serial number of the reagent (R1/R3 reagent) to be the pairing reagent does not exist in the reagent information of "j" (No).

In step S1009, the control unit 4a determines whether or not the R1/R3 reagent identified by the serial number of the reagent to be the pairing reagent is set in the reagent holder. The control unit 4a advances the process to step S1009-1 when determining that the R1/R3 reagent identified by the serial number of the reagent to be the pairing reagent is set in the reagent holder (Yes), adds the information of "usable" to the reagent information of "j" and advances the process to step S1011. The control unit 4a advances the process to step S1010 when determining that the R1/R3 reagent identified by the serial number of the reagent to be the pairing reagent is not set in the reagent holder (No), and adds the information of "not usable" to the reagent information of "j" in step S1010.

In step S1011, the control unit 4a determines whether or not "j" is equal to "N". The control unit 4a advances the process to step S1017 when determining that "j" is equal to "N" (Yes), advances the process to step S1012 when determining that "j" is not equal to "N" (No), and increments "j" in step S1012 and returns the process to step S1007.

In step S1013, the control unit 4a determines whether or not the items (measurement items) of "i" and "j" match. The control unit 4a advances the process to step S1014 when determining that the items (measurement items) of "i" and "j" match (Yes), advances the process to step S1013-1 when determining that the items (measurement items) of "i" and "j" do not match (No), adds information of "not usable" to the reagent information of "i" and "j", and returns the process to step S1011.

In step S1014, the control unit 4a determines whether or not the lot numbers of "i" and "j" match. The control unit 4a advances the process to step S1015 when determining that the lot numbers of "i" and "j" match (Yes), advances the process to step S1013-1 when determining that the lot numbers of "i" and "j" do not match (No), adds information of "not usable" to the reagent information of "i" and "j", and returns the process to step S1011.

In step S1015, the control unit 4a adds the serial number of "j" serving as the serial number of the pairing reagent and the information of "usable" to the reagent information of "i".

Although the flowchart is omitted, the second usable reagent determining process described in step S710 is not a process of determining whether all the reagents set in the reagent holder are usable as in the first usable reagent determining process, but is a process of determining usability only on the reagent newly set through replacement and addition of reagent through a process similar to the first usable reagent determining process. In the second usable reagent determining process, when the reagent information of the newly added R1/R3 reagent exists in the reagent DB, if the serial number of the reagent to be the pairing reagent is included in the reagent information, determination is made on whether or not the R2 reagent identified by the serial number is set in the reagent holder. If the reagent information does not exist in the reagent DB, determination is made on whether the R2 reagent same as the set R2 reagent in items and lot number exists, and if a pair is found, the relative reagent is registered as the usable reagent.

In step S1016, the control unit 4a adds the serial number of "i" serving as the serial number of the pairing reagent of "j" and the information of "usable" to the reagent information of "j".

In step S1017, the control unit 4a determines whether or not "i" is equal to "N". The control unit 4a advances the process to step S312 when determining that "i" is equal to "N" (Yes), advances the process to step S1018 when determining that "i" is not equal to "N" (No), and increments "i" in step S1018 and returns the process to step S1002.

Priority Determining Process

Figure 31:
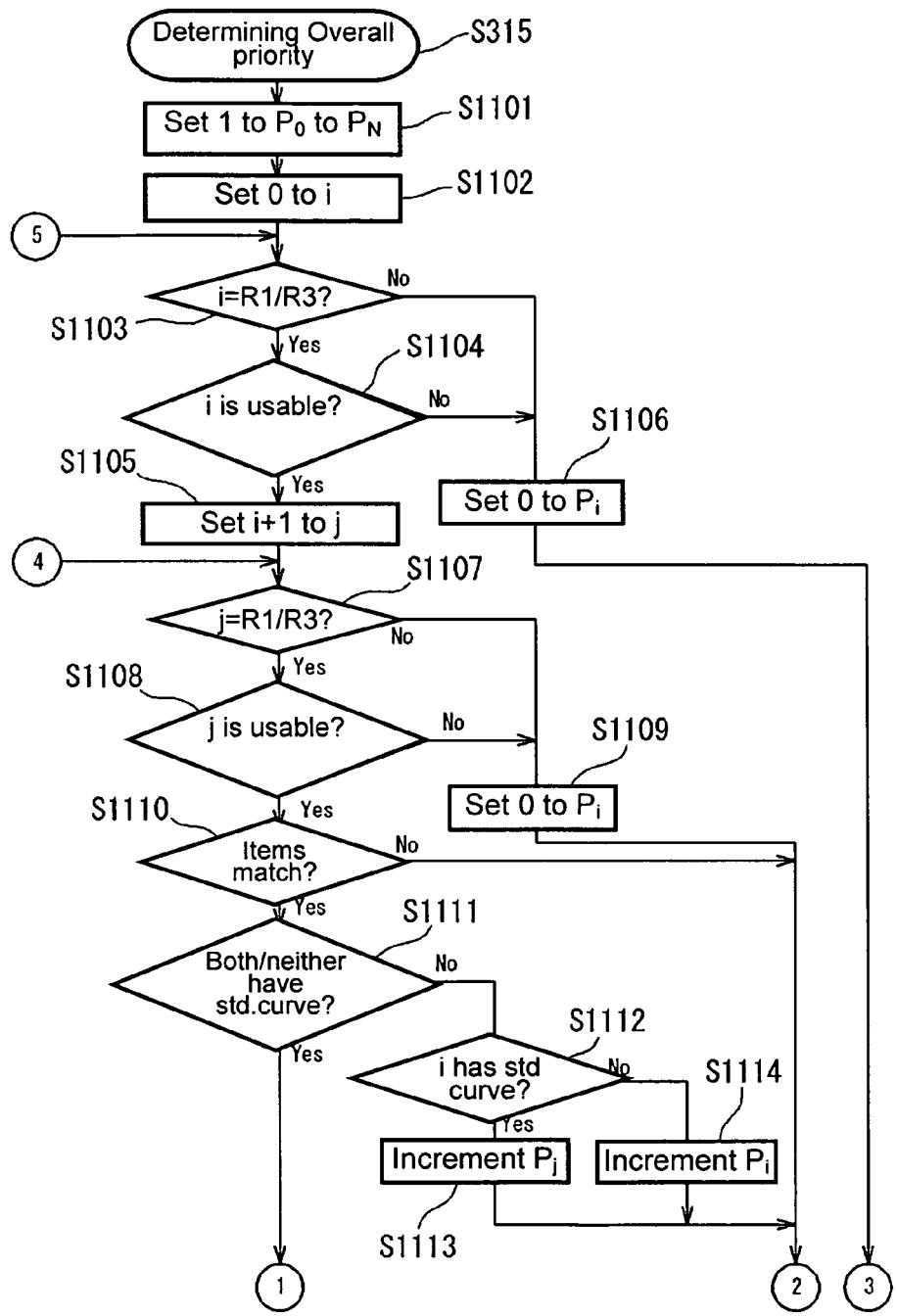
FIG. 31 is a view showing a flow of an overall priority determining process.
Figure 32:
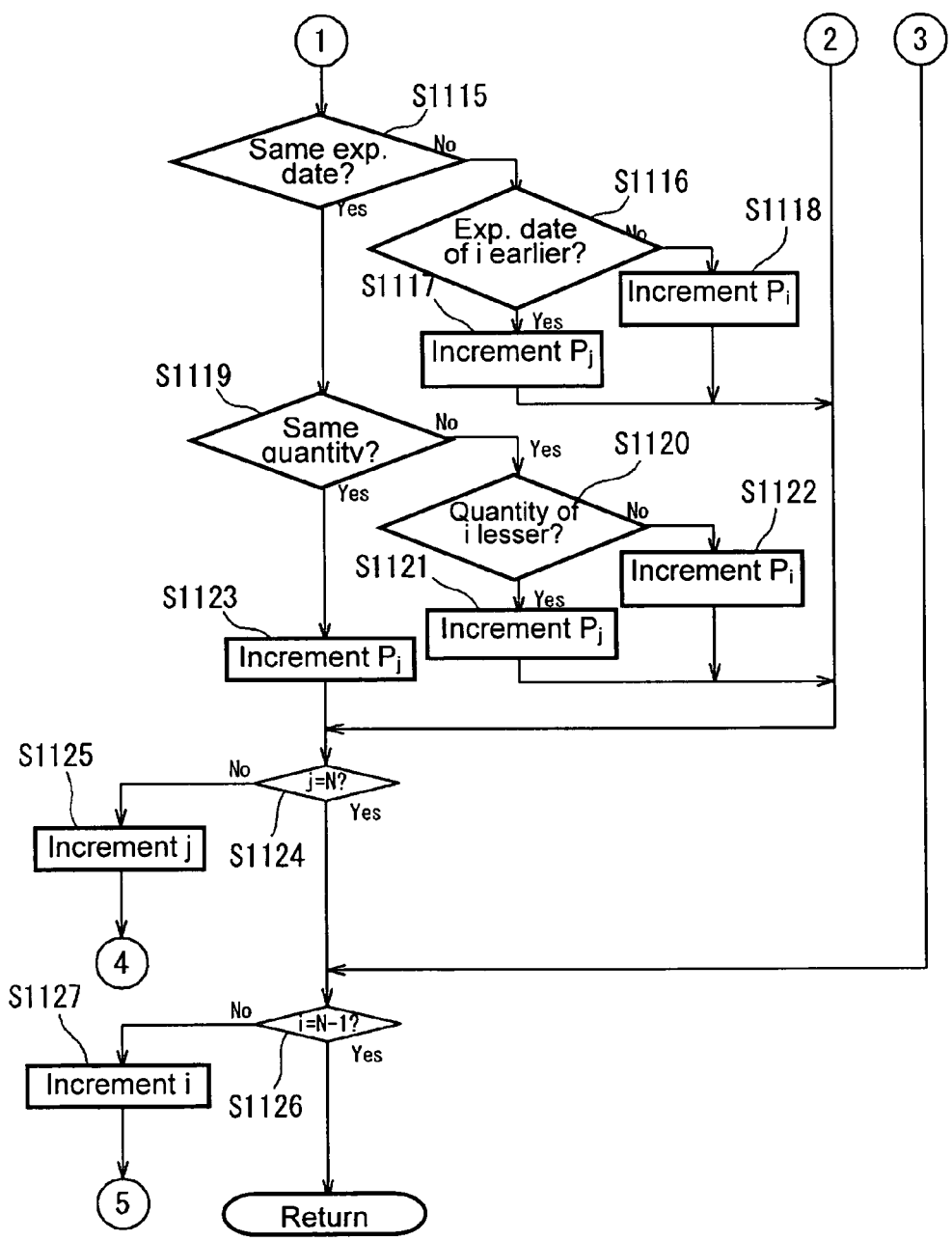
FIG. 32 is a view showing a flow of an overall priority determining process.

The flow of the priority determining process in steps S315, S406, S715, and S904 is shown in FIGS. 31 and 32. In the flowchart shown in FIGS. 31 and 32 as well, "i" and "j" indicate the number (reagent ID) of the reagent set position, and "N" indicates the maximum number of reagent sets, that is, the maximum value of the reagent ID. $P_0$ to $P_N$ are parameters indicating the priority, where the subscript "0" indicates "not usable", "1" indicates priority number one, "2" indicates priority number 2, . . . and "N" indicates priority number N.

First, in step S1101, the control unit 4a sets "1" to $P_0$ to $P_N$, and then the control unit 4a sets "0" to "i" in step S1102.

In step S1103, the control unit 4a determines whether or not "i" is R1/R3 reagent. The control unit 4a advances the process to step S1104 when determining that "i" is the R1/R3 reagent (Yes), and advances the process to step S1106 when determining that "i" is not the R1/R3 reagent (No).

In step S1104, the control unit 4a determines whether or not "i" is usable. The control unit 4a advances the process to step S1105 when determining that "i" is usable (Yes), and advances the process to step S1106 when determining that "i" is not usable (No).

In step S1105, the control unit 4a sets "i+1" to "j". In step S1106, on the other hand, the control unit 4a sets "0" to $P_i$.

In step S1107, the control unit 4a determines whether or not "j" is R1/R3 reagent. The control unit 4a advances the process to step S1108 when determining that "j" is the R1/R3 reagent (Yes), and advances the process to step S1109 when determining that "i" is not the R1/R3 reagent (No).

In step S1108, the control unit 4a determines whether or not "j" is usable. The control unit 4a advances the process to step S1110 when determining that "j" is usable (Yes), and advances the process to step S1109 when determining that "j" is not usable (No).

In step S1110, the control unit 4a determines whether the items (measurement items) of "i" and "j" match. The control unit 4a advances the process to step S1111 when determining that the items (measurement items) of "i" and "j" match (Yes), and advances the process to step S1124 when determining that the items (measurement items) of "i" and "j" do not match (No). In step S1109, on the other hand, the control unit 4a sets "0" to $P_j$.

In step S1111, the control unit 4a determines whether or not a standard curve exists for both or a standard curve does not exist for both based on the reagent information for the two R1/R3 reagents in which the measurement items matched in step S1110. That is, for each of the two R1/R3 reagents in which the measurement items matched, whether or not a standard curve corresponding to the lot number of the reagent exists is determined, and determination is made on whether the standard curve exits for both R1/R3 reagents, the standard curve does not exist for both R1/R3 reagents, or the standard curve exists for only one R1/R3 reagent. The control unit 4a advances the process to step S115 when determining that the standard curve exists for both or the standard curve does not exist for both (Yes), and advances the process to step S1112 when determining that the standard curve exists only for one of the two (No).

In step S1112, the control unit 4a determines whether or not "i" has a standard curve. The control unit 4a advances the process to step S1113 when determining that the "i" has the standard curve (standard curve corresponding to the lot number of the reagent of "i" exists) (Yes), and increments $P_j$ in step S1113. The control unit 4a advances the process to step S1114 when determining that the "i" does not have the standard curve (standard curve corresponding to the lot number of the reagent of "i" does not exist) (No), and increments "$P_i$" in step S1114.

In step S1115, the control unit 4a determines whether or not the expiration date of both reagents of "i" and "j" are the same based on the reagent information. The control unit 4a advances the process to step S1119 when determining that the expiration date of both reagents are the same (Yes), and advances the process to step S1116 when determining that the expiration date of both reagents are not the same (No).

In step S1116, the control unit 4a determines whether the expiration date of "i" is earlier than the expiration date of "j" based on the reagent information regarding the expiration date of both reagents of "i" and "j". The control unit 4a advances the process to step S1117 when determining that the expiration date of "i" is earlier than the expiration date of "j" (Yes), increments "$P_j$" in step S1117, and advances the process to step S1124. The control unit 4a advances the process to step S1118 when determining that the expiration date of "i" is not earlier than the expiration date of "j" (No), increments "$P_i$" in step S1118, and advances the process to step S1124.

In step S1119, the control unit 4a determines whether or not the remaining quantity of both reagents of "i" and "j" are the same based on the reagent information. The control unit 4a advances the process to step S1123 when determining that the remaining quantity of both reagents are the same (Yes), and advances the process to step S1120 when determining that the remaining quantity of both reagents are not the same (No).

In step S1120, the control unit 4a determines whether the remaining quantity of "i" is less than the remaining quantity of "j" based on the reagent information regarding the remaining quantity of both reagents of "i" and "j". The control unit 4a advances the process to step S1121 when determining that the remaining quantity of "i" is less than the remaining quantity of "j" (Yes), increments "$P_j$" in step S1121, and advances the process to step S1124. The control unit 4a advances the process to step S1122 when determining that the remaining quantity of "i" is not less than the remaining quantity of "j" (No), increments "$P_i$" in step S1122, and advances the process to step S1124.

In step S1124, the control unit 4a determines whether "j"="N". The control unit 4a advances the process to step S1126 when determining that "j"="N" (Yes), advances the process to step S1125 when determining "j"="N" is not met (No), increments "j" in step S1125, and returns the process to step S1107.

In step S1126, the control unit 4a determines whether "i"="N−1". The control unit 4a terminates the process when determining that "i"="N−1" (Yes), advances the process to step S1127 when determining "i"="N−1" is not met (No), increments "i" in step S1127, and returns the process to step S1103.

The priority determining process described above will now be described based on specific examples. Suppose the priority of use is to be determined for the eight reagents shown in table according to the flowchart shown in FIGS. 31 and 32. In table 1, the reagent which reagent ID is at the position of "2" does not have information of the serial number of the reagent to be the pairing reagent configuring the measurable reagent set, and the reagents at other positions have information of the serial number of the reagent to be the pairing reagent.

TABLE 1

| Reagent ID | Item | Type | Standard Curve | Expiration Date | Remaining Quantity | Usability |
|---|---|---|---|---|---|---|
| 0 | HB$_S$Ag | R1/R3 | Yes | Mar. 30, 2007 | 80 | Usable |
| 1 | HTLV | R1/R3 | Yes | Apr. 5, 2007 | 25 | Usable |
| 2 | HB$_S$Ag | R1/R3 | No | Apr. 1, 2007 | 100 | Not Usable |
| 3 | HCV | R1/R3 | No | Apr. 10, 2007 | 100 | Usable |
| 4 | HB$_S$Ag | R2 | No | Mar. 30, 2007 | 100 | Usable |
| 5 | HB$_S$Ag | R1/R3 | Yes | Mar. 30, 2007 | 13 | Usable |
| 6 | HCV | R1/R3 | No | Apr. 11, 2007 | 70 | Usable |
| 7 | HB$_S$Ag | R1/R3 | No | Mar. 29, 2007 | 25 | Usable |

First, in step S1101, $P_0$ to $P_7$ are set to "1". Then, "i" is set to "0" (Step S1101). The reagent of "0" is the R1/R3 reagent, and the serial number of the reagent to be the pairing reagent exists, and thus "1" is set to "j" in step S1105. The reagent of "1" is the R1/R3 reagent and the serial number of the reagent to be the pairing reagent exists, but the item of "0" is HB$_S$Ag, whereas the item of "1" is HTLV, and thus the items of both reagents do not match, and thus determination is made as "No" in step S1110. After step S1124 and step S1125, "j" is incremented to "2". Therefore, at this stage, there is no change in $P_0$ and $P_1$, and is still "1" as initially set.

The process is returned to step S1107, and determination is made on whether or not the reagent of "2" is R1/R3 reagent. The reagent of "2" is R1/R3 reagent but the serial number of the reagent to be the pairing reagent does not exist, and thus $P_2$ is set to "0" in step S1109. After step S1124 and step S1125, "j" is incremented to "3".

The process is returned to step S1107, and determination is made on whether or not the reagent of "3" is R1/R3 reagent. The reagent of "3" is R1/R3 reagent and the serial number of the reagent to be the pairing reagent exists, but the item of "0" is HB$_S$Ag whereas the item of "3" is HCV, and thus the items of both reagents do not match, and determination is made as "No" in step S1110. After step S1124 and step S1125, "j" is incremented to "4". Therefore, at this stage, there is no change in $P_0$ and $P_3$, and is still "1" as initially set.

The process is returned to step S1107, and determination is made on whether or not the reagent of "4" is R1/R3 reagent. The reagent of "4" is R2 reagent and not R1/R3 reagent, and thus determination is made as "No" in step S1107. In step S1109, $P_4$ is set to "0". $P_1$ is not changed and remains "1". After step S1124 and step S1125, "j" is incremented to "5".

The process is returned to step S1107, and determination is made on whether or not the reagent of "5" is R1/R3 reagent. The reagent of "5" is R1/R3 reagent and the serial number of the reagent to be the pairing reagent exists, and furthermore, the item match with the reagent of "0", and thus the process is advanced to step S1111. The reagent of "0" and the reagent of "5" both have a standard curve corresponding to the reagent lot number, and the expiration date (30/3/2007) is the same, and thus the process is advanced to step S1119 and determination is made on whether or not the remaining quantity is the same. As a result of the determination, the reagent of "5" has lesser remaining quantity than the reagent of "0", and thus the determination is "No" in step S1120, and $P_0$ is incremented to "2" in step S1122. $P_5$ is not changed and remains "1". After step S1124 and step S1125, "j" is incremented to "6".

The process is returned to step S1107, and determination is made on whether or not the reagent of "6" is R1/R3 reagent. The reagent of "6" is R1/R3 reagent and the serial number of the reagent to be the pairing reagent exists, but the item of "0" is HB$_S$Ag whereas the item of "3" is HCV, and thus the items of both reagents do not match, and thus determination is made as "No" in step S1110. After step S1124 and step S1125, "j" is incremented to "7". Therefore, at this stage, there is no change in $P_0$ and $P_6$, and $P_0$=2 and $P_6$=1.

The process is returned to step S1107, and determination is made on whether or not the reagent of "7" is R1/R3 reagent. The reagent of "7" is R1/R3 reagent and the serial number of the reagent to be the pairing reagent exists, and furthermore, the item match with the reagent of "0", and thus the process is advanced to step S1111. In step S1111, the reagent of "0" has a standard curve corresponding to the lot number, but the reagent of "7" does not have a standard curve corresponding to the reagent lot number, and thus the determination of step S1111 becomes "No", and the process is advanced to step S1112. The reagent of "0" has a standard curve corresponding to the lot number, and thus the process is advanced to step S1113, and $P_7$ is incremented to "2". $P_0$ is not changed and remains "2".

The "i" is set to "1" through the steps S1124, S1126, and S1127, and then the process is returned to step S1103.

In step S1103, determination is made on whether or not the reagent of "1" is R1/R3 reagent. The reagent of "1" is R1/R3 reagent and the serial number of the reagent to be the pairing reagent exists, and thus "j" is set to "2" in step S1105. The reagent of "2" is R1/R3 reagent and the serial number of the reagent to be the pairing reagent exists, but the item of "1" is HTLV whereas the item of "2" is HB$_S$Ag, and thus the item of both reagents does not match, and thus the determination is made as "No" in step S1110. After step S1124 and step S1125, "j" is incremented to "3".

The process is similarly performed until "i"=6 and "j"=7. The description thereof will be omitted, but as a result of the process, P0=2, P1=1, P2=0, P3=1, P4=0, P5=1, P6=2, and P7=3, and the priority of HBSAg becomes lower in the order of reagent of "5", reagent of "0", and reagent of "7". That is, first the reagent of "5" is used, then the reagent of "0" is used, and lastly, the reagent of "7" is used. The priority of HCV becomes lower in the order of reagent "3" and reagent of "6".

In the present embodiment, description has been made with the priority determining process (step S315, step S715, and step S904) executed by the control unit 4a and the priority determining process (step S406) executed by the body control unit 2a as the same process, but the priority determining process executed by the control unit 4a and the priority determining process executed by the body control unit 2a may be different. In the body control unit 2a, the priority of the reagent is determined for every measurement, and the reagent having the highest priority is used to perform the measurement. Therefore, when two or more of reagents of the same items are set, determination is made on whether or not the standard curve corresponding to the lot number exists for each reagent, where if the corresponding standard curve exists only for one reagent, the relevant reagent is used and the process is terminated without determining the priority of the remaining reagents.

In the present embodiment, the standard curve is created for every lot number of the reagent, and one standard curve is shared with a plurality of reagents having the same items and the same lot numbers. However, the present invention is not limited thereto. The standard curve may be created for every serial number of the reagent, that is, for every reagent, and the standard curve and the reagent may be corresponded one to one. In this case, the serial number of the reagent used in the measurement of the calibrator is stored in the standard curve database in correspondence to the standard curve generated from the measurement data. In the usage priority determination of the reagent, determination is made on whether or not the standard curve corresponding to the respective serial number exists for two reagents of the same items, and the priority is determined based on the determination result.

Therefore, according to the sample analyzer of one embodiment of the present invention, the analysis result can be rapidly and reliably obtained, and waste of reagent and sample can be eliminated.

In the sample analyzer according to one embodiment of the present invention, if a plurality of the same reagents exists in the reagent holder, the reagent created with the standard curve is used first. If the standard curve does not exist, the analysis result cannot be obtained, and for example, determination on whether or not re-examination is necessary cannot be made, but if the reagent which standard curve exists is used, the analysis result can be rapidly and reliably obtained, and determination of re-examination can be smoothly performed. Due to reasons of problems in terms of reagent management, error may occur on the standard curve itself. In this case, measurement is performed using the reagent which standard curve is not created, and when the existence of error in the standard curve of the relevant reagent becomes apparent afterwards, the measurement performed up to that point as well as the samples and the reagents used for the measurement become a waste. When measurement is performed using the reagent which standard curve exists, such measurement and sample will not be a waste.

It should be apparent to those skilled in the art that the present invention may be embodied in many other specific forms without departing from the spirit or scope of the invention. Therefore, the present invention is not to be limited to the details given herein, but may be modified within the scope and equivalence of the appended claims.

What is claimed is:

1. A sample analyzer comprising:
   a reagent container holder for holding a first reagent container accommodating a first reagent and a second reagent container accommodating a second reagent;
   a measurement specimen preparer for mixing a sample with at least one of the first reagent and the second reagent, thereby preparing a measurement specimen;
   a memory for storing standard curve data corresponding to a reagent to be used by the measurement specimen preparer for preparing a measurement specimen;
   a measuring unit for measuring the measurement specimen thereby obtaining measurement data;
   a processor; and
   a non-transitory computer readable storage medium having stored therein data representing instructions executable by the processor, the storage medium including
   a first set of instructions to process the measurement data based on the standard curve data, thereby obtaining an analysis result, and a second set of instructions to determine a reagent to be used for the measuring between the first reagent and the second reagent based on information regarding standard curve data stored in the memory when the first reagent and the second reagent are of the same type.

2. The sample analyzer according to claim 1, wherein second set of instructions determines the first reagent as a reagent to be used when standard curve data corresponding to the first reagent is stored in the memory, and standard curve data corresponding to the second reagent is not stored in the memory.

3. The sample analyzer according to claim 1, wherein the first reagent container and the second reagent container each have an identifier, respectively;
   the sample analyzer further comprises a reading unit for obtaining reagent identifying information by reading the identifier;
   the memory stores the standard curve data in correspondence to the reagent identifying information of the reagent corresponding to the standard curve data; and
   the second set of instructions determines whether the standard curve data corresponding to the reagent identified by the reagent identifying information corresponding to the first reagent container and the standard curve data corresponding to the reagent identified by the reagent identifying information corresponding to the second reagent container are stored in the memory when the first reagent and the second reagent are of the same type.

4. The sample analyzer according to claim 3, wherein the reagent identifying information includes a lot number of the reagent.

5. The sample analyzer according to claim 4, wherein the first set of instructions obtains the analysis result using common standard curve data with respect to measurement data obtained using the first reagent and measurement data obtained using the second reagent when the first reagent and the second reagent are of the same type and the lot numbers of the first reagent and the second reagent are the same.

6. The sample analyzer according to claim 1, wherein the second set of instructions determines usage order of the first reagent and the second reagent when the first reagent and the second reagent are of the same type.

7. The sample analyzer according to claim 6, wherein the second set of instructions determines the order so that the first reagent is used before the second reagent when standard curve data corresponding to the first reagent is stored in the memory and standard curve data corresponding to the second reagent is not stored in the memory.

8. The sample analyzer according to claim 6, further comprising a display for displaying a reagent list in which information related to the reagent is listed according to the usage order determined by the means second set of instructions.

9. The sample analyzer according to claim 1, wherein the storage medium further includes:
   a third set of instructions to create the standard curve data;
   a fourth set of instructions to accept validation of using the standard curve data created by the third set of instructions; wherein
   the memory stores the validated standard curve data when validation of the standard curve data is accepted by the fourth set of instructions.

10. The sample analyzer according to claim 1, further comprising a reagent information memory for storing reagent information for each reagent on the reagent holder, the reagent information comprising information indicating whether or not the standard curve data corresponding to the reagent is stored in the memory; wherein
   the second set of instructions determines the reagent to be used for the measuring between the first reagent and the second reagent based on the reagent information stored in the reagent information memory when the first reagent and the second reagent are of the same type.

11. The sample analyzer according to claim 1, further comprising a fifth set of instructions to manage expiration date of the reagent; wherein
   the second set of instructions determines the reagent to be used for the measuring between the first reagent and the second reagent based on expiration date of the first reagent and expiration date of the second reagent managed by the fifth set of instructions when the first reagent and the second reagent are of the same type.

12. The sample analyzer according to claim 1, further comprising a sixth set of instructions to manage remaining quantity of the reagent; wherein the second set of instructions determines the reagent to be used for the measuring between the first reagent and the second reagent based on remaining quantity of the first reagent and remaining quantity of the second reagent managed by the sixth set of instructions when the first reagent and the second reagent are of the same type.

* * * * *

UNITED STATES PATENT AND TRADEMARK OFFICE
CERTIFICATE OF CORRECTION

| | |
|---|---|
| PATENT NO. | : 8,071,029 B2 |
| APPLICATION NO. | : 12/079798 |
| DATED | : December 6, 2011 |
| INVENTOR(S) | : Yuji Wakamiya et al. |

It is certified that error appears in the above-identified patent and that said Letters Patent is hereby corrected as shown below:

<u>In the Claims</u>

In column 30, claim 8, line 38, after "determined by the" delete "means".

Signed and Sealed this
Twenty-ninth Day of May, 2012

David J. Kappos
*Director of the United States Patent and Trademark Office*